United States Patent
Chi et al.

(10) Patent No.: US 12,334,193 B2
(45) Date of Patent: Jun. 17, 2025

(54) METHOD AND SYSTEM FOR PREDICTING AFFINITY BETWEEN DRUG AND TARGET

(71) Applicant: Alibaba (China) Co., Ltd., Hangzhou (CN)

(72) Inventors: Ying Chi, Beijing (CN); Peiran Jiang, Hangzhou (CN)

(73) Assignee: Alibaba (China) Co., Ltd. (CN)

( * ) Notice: Subject to any disclaimer, the term of this patent is extended or adjusted under 35 U.S.C. 154(b) by 514 days.

(21) Appl. No.: 17/592,924

(22) Filed: Feb. 4, 2022

(65) Prior Publication Data

US 2022/0284990 A1    Sep. 8, 2022

(30) Foreign Application Priority Data

Mar. 2, 2021  (CN) .......................... 202110231222.4

(51) Int. Cl.
| | |
|---|---|
| *G16C 20/30* | (2019.01) |
| *G06N 3/045* | (2023.01) |
| *G06N 20/20* | (2019.01) |
| *G16C 20/50* | (2019.01) |
| *G16C 20/70* | (2019.01) |

(52) U.S. Cl.
CPC .............. *G16C 20/30* (2019.02); *G06N 3/045* (2023.01); *G06N 20/20* (2019.01); *G16C 20/50* (2019.02); *G16C 20/70* (2019.02)

(58) Field of Classification Search
CPC ........ G16C 20/30; G16C 20/50; G16C 20/70; G06N 3/045; G06N 20/20
See application file for complete search history.

(56) References Cited

U.S. PATENT DOCUMENTS

| | | | |
|---|---|---|---|
| 7,751,988 B2 | 7/2010 | Kita | |
| 8,036,867 B2 | 10/2011 | Prakash | |
| 10,877,035 B2 | 12/2020 | Birnbaum | |
| 2004/0072162 A1* | 4/2004 | Fomsagaard | ........ C07K 14/005 435/7.1 |
| 2019/0304568 A1 | 10/2019 | Wei | |
| 2022/0246233 A1* | 8/2022 | Morrone | ................ G16B 15/30 |

FOREIGN PATENT DOCUMENTS

| | | | |
|---|---|---|---|
| CN | 106575320 | 4/2017 | |
| CN | 108288106 A * | 7/2018 | ............. G06Q 10/04 |
| CN | 110767266 | 2/2020 | |
| CN | 110957002 | 4/2020 | |

(Continued)

OTHER PUBLICATIONS

Machine translation of CN-108288106-A, downloaded Sep. 2024 (Year: 2024).*

(Continued)

*Primary Examiner* — John C Kuan
(74) *Attorney, Agent, or Firm* — Van Pelt, Yi & James LLP

(57) ABSTRACT

Prediction of an affinity between a drug and a target is disclosed. The drug and the target for interacting with the drug are acquired. An interaction is caused between the drug and the target to determine the compound. Topological structure graphs for labeling spatial characteristics of atoms in the compound are computed. An affinity between the drug and the target based on the topological structure graphs is determined.

19 Claims, 17 Drawing Sheets

(56) References Cited

FOREIGN PATENT DOCUMENTS

| CN | 111445945 | 7/2020 |
|---|---|---|
| CN | 112201313 | 1/2021 |

OTHER PUBLICATIONS

Cang et al., "Integration of element specific persistent homology and machine learning for protein-ligand binding affinity prediction" Int J Numer Meth Biomed Engng. 2018 (Year: 2018).*
Lin et al., DeepGS: Deep Representation Learning of Graphs and Sequences for Drug-Target Binding Affinity Prediction ECAI 2020 (Year: 2020).*
M. Wang et al., "A topology-based network tree for the prediction of protein-protein binding affinity changes following mutation" Nature Machine Intelligence, vol. 2, 2020 (Year: 2020).*
Ozturk et al., "DeepDTA: deep drug-target binding affinity prediction" Bioinformatics, 34, 2018, i821-i829 (Year: 2018).*
R. Wang et al., "Persistent spectral graph" Int J Numer Meth Biomed Engng. 2020 (Year: 2020).*
Liu, et al. "Hypergraph-based persistent cohomology (HPC) for molecular representations in drug design." Briefings in Bioinformatics 22.5 (2021): bbaa411.
Meng et al. "Persistent spectral based machine learning (PerSpect ML) for drug design." arXiv preprint arXiv:2002.00582 (2020).

\* cited by examiner

METHOD AND SYSTEM FOR PREDICTING AFFINITY BETWEEN DRUG AND TARGET

CROSS REFERENCE TO OTHER APPLICATIONS

This application claims priority to People's Republic of China Patent Application No. 202110231222.4 entitled A METHOD, MEANS, AND DEVICE FOR PREDICTING THE AFFINITY BETWEEN A DRUG AND A TARGET filed Mar. 2, 2021 which is incorporated herein by reference for all purposes.

FIELD OF THE INVENTION

The present invention relates to a method and a system for predicting an affinity between a drug and a target.

BACKGROUND OF THE INVENTION

As artificial intelligence (AI) continues to develop, drug design based on AI has potential to change drug design and discovery. Molecular representation is beneficial to all AI-based drug design models. Typically, two types of molecular representations exist. The first type of molecular representation is feature engineering, which can compute a molecule's structural, physical, chemical, and biological characteristics and use the characteristics as molecular descriptors for learning models. Typically, molecular representation is a group of predefined manual features, including molecular formulas, fragments, motifs, topological features, geometric features, conformation properties, hydrophobicity, electronic properties, steric properties, and other such information. A large number of molecular descriptors have already been proposed and are used in quantitative structure-activity relationship (QSAR) and learning models. The second type of molecular representation includes using end-to-end representation learning with a 3D convolutional neural network and a graph neural network where representation learning corresponds to an AI technique. In these models, the molecular representation is network data in which each cell includes molecular features, or the molecular representation is a graph in which molecular attributes are embedded at the vertices and edges of the graph.

Recently, progress has been made in geometry-based molecular characterization in drug design. In contrast to past models, molecular descriptors and fingerprints are defined as geometric, topological, and combined invariants in differential geometry, algebraic topology, and algebraic graph theory. Applying mathematical forms of molecular representation to drug design merits research.

BRIEF DESCRIPTION OF THE DRAWINGS

Various embodiments of the invention are disclosed in the following detailed description and the accompanying drawings.

DETAILED DESCRIPTION

Figure 1:
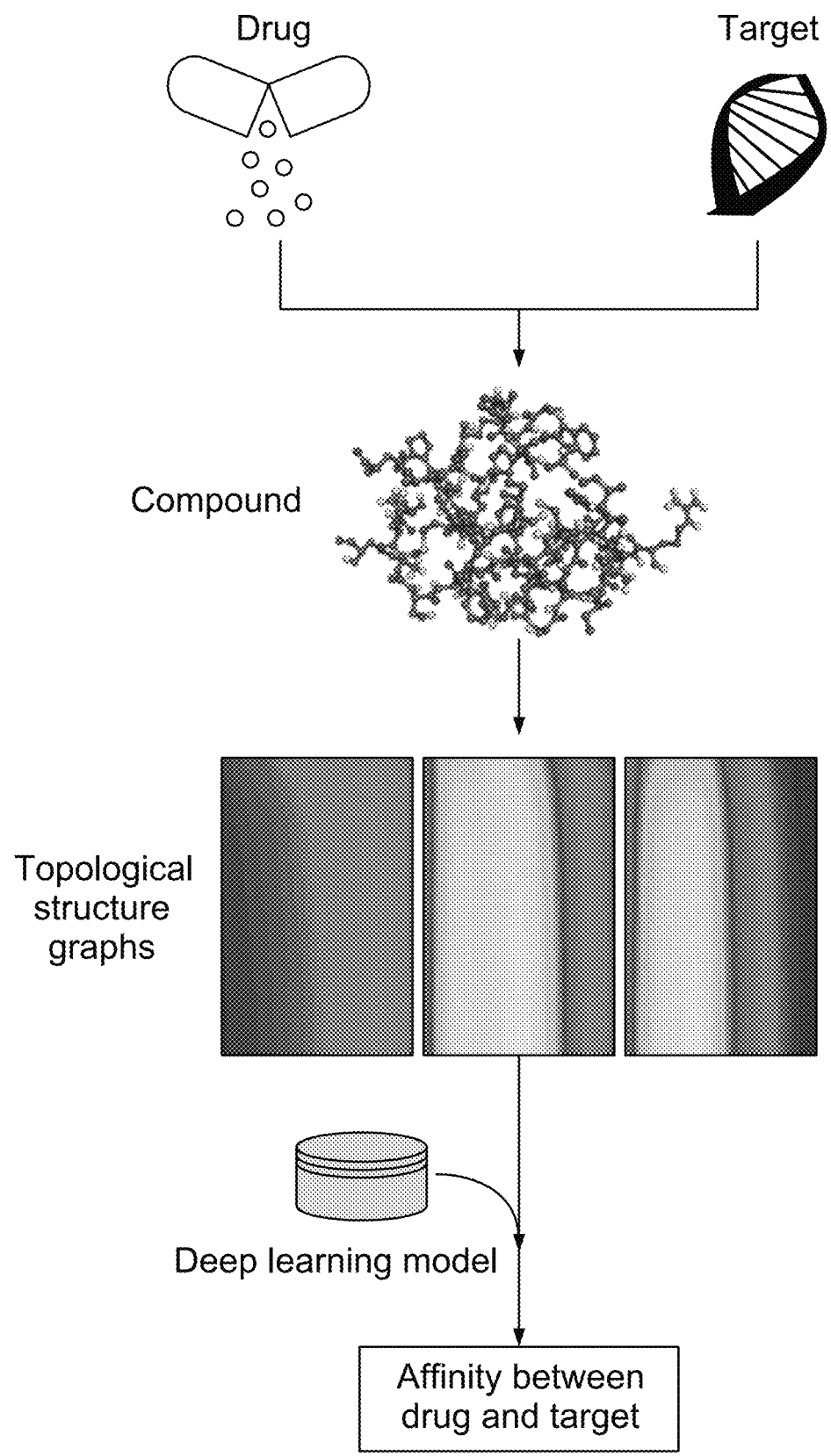
FIG. 1 is a schematic diagram of an example of a process for predicting an affinity between a drug and a target.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Definition of Terms

Persistent spectral graph (PerSpect graph): a graph structure for labeling persistence and extent of change of topological features.

Simplicial complex: Given K=(V, S), where V is a set of vertices and S is a subset of $2^V$. In the event that the following are satisfied: (1) from $\tau' \subset \tau$, $\tau \in S$, $\tau' \in S$ can be derived; and (2) $\tau \cap \pi = \sigma$ or $\tau \cap \pi$ is the common face of $\tau'$ and $\tau$, then K=(V, S) can be called a simplicial complex.

Persistent spectral simplicial complex (PerSpect simplicial complex): a topological structure graph corresponding to simplices, where, given K=(V, S), in the event that any subset of $2^V$ is included in S, then K=(V, S) can be called a simplex.

Persistent spectral hypergraph (PerSpect hypergraph): a graph structure for labeling the persistence and extent of change of topological features of a hypergraph.

Recently, progress has been made in geometry-based molecular characterization in drug design. In contrast to past models, the molecular descriptors and fingerprints are defined as geometric, topological, and combined invariants in differential geometry, algebraic topology, and algebraic graph theory. These geometry-based molecular characterization models can notably increase performance of machine learning models in each step of drug design, including: protein-ligand binding affinity prediction, protein stability change upon mutation prediction, toxicity prediction, solvation free energy prediction, partition coefficient and aqueous solubility, binding pocket detection, and drug discovery.

Because these mathematical models have been helpful in drug design, a drug-target affinity prediction process based on persistent spectral graph (PerSpect) theory is disclosed. This prediction process can be applicable to PerSpect graphs, PerSpect simplicial complexes, and PerSpect hypergraphs. As an example, the executing entity for the prediction process described above is a predicting system which can be communicatively connected to a client.

The client can be any computing device having a certain computing capability. The structure of the client can include: at least one processor. The number of processors can be determined by the client configuration and type. The client can include memory. The memory can be volatile, such as RAM, or non-volatile, such as read-only memory (ROM) or flash memory. In some embodiments, the client can simultaneously include both types. The memory typically stores an operating system (OS) and one or more applications. The memory can also store program data. In addition to processors and memory, the client can also include some basic configurations such as network card chips, I/O buses, display components, and peripheral devices. In some embodiments, peripheral devices include, for example, keyboards, mice, styluses, and printers. Other peripheral devices are common knowledge in the art and need not be discussed in detail here. In some embodiments, the client can be a PC (personal computer) terminal or hand-held terminal (such as a smart phone or a tablet).

The "prediction system" can refer to a device that provides computing and processing services in a network virtual environment. The prediction system typically refers to a system that uses networks to conduct information planning and that predicts an affinity between a drug and a target. In its physical implementation, the system for predicting an affinity between a drug and a target can be any device that can provide computing services, respond to service requests, and perform processing. In some embodiments, the affinity is measured using a Pearson correlation value. For example, the prediction system is a cluster server, conventional server, cloud server, cloud host, or a virtual center. The system for predicting an affinity between a drug and a target is mainly composed of processors, hard drives, memory, and system buses. The architecture of the prediction system can be similar to that of a general-purpose computer.

In some embodiments, the client connects through a network with the drug-target affinity prediction system. The network connection can he a wireless or wired connection. The client and the drug-target affinity prediction system can be communicatively connected. The network system of the mobile network can be any one of the following: 2G (GSM), 2.5G (GPRS), 3G (WCDMA, TD-SCDMA, CDMA2000, UTMS), 4G (LTE), 4G+ (LTE+), and/or WiMax.

In some embodiments, the client acquires a drug and a target for interacting with the drug. In some embodiments, the drug refers to the drug in need of affinity prediction. In some embodiments, the drug and the target that interacts with the drug are pre-allocated. In some embodiments, the drug and the target that interacts with the drug are input or designated by a user. A person of ordinary skill in the art can adopt another approach to acquire a drug and an interacting target, and will not be further discussed for conciseness. After acquiring the drug and the target that interacts with the drug, the drug and the target that interacts with the drug can be sent to the prediction system so that the prediction system can perform prediction processing on the drug-target affinity.

FIG. 1 is a schematic diagram of an example of a process for predicting an affinity between a drug and a target. In some embodiments, the drug-target affinity prediction process is configured to acquire a drug and a target for interacting with the drug. After the drug and the target are acquired, an interaction between the drug and the target can be caused to obtain a compound and topological structure graphs for labeling spatial characteristics of atoms in the compound can be computed. The obtained topological structure graphs can include at least one group. Each group of topological structure graphs can include multiple topological structure graphs. In some embodiments, the topological structure graphs include at least one of the following: a persistent spectral graph, a persistent spectral simplicial complex, change features of the persistent spectral simplicial complex, and/or a persistent spectral hypergraph. In some embodiments, the persistent spectral graph labels the persistence and extent of change of topological features, and the persistent spectral hypergraph labels the persistence and extent of change of topological features of a hypergraph. After acquiring the topological structure graphs, the topological structure graphs can be input into a pretrained deep learning model. The deep learning model can analytically process the topological structure graphs and thus can determine the affinity between the drug and the target.

The process can include: acquiring a drug and a target for interacting with the drug, causing a drug-target interaction to determine the compound, computing topological structure graphs for labeling spatial characteristics of atoms in the compound, and determining an affinity between the drug and the target based on the topological structure graphs. The process can effectively implement the determination of drug-target affinity that can be based on topological structure graphs corresponding to a compound. Not only is the affinity determined accurately and reliably, but also the process can determine the stability of drug-target action based on the predicted affinity and thus increase the utility of the prediction process.

Figure 2:
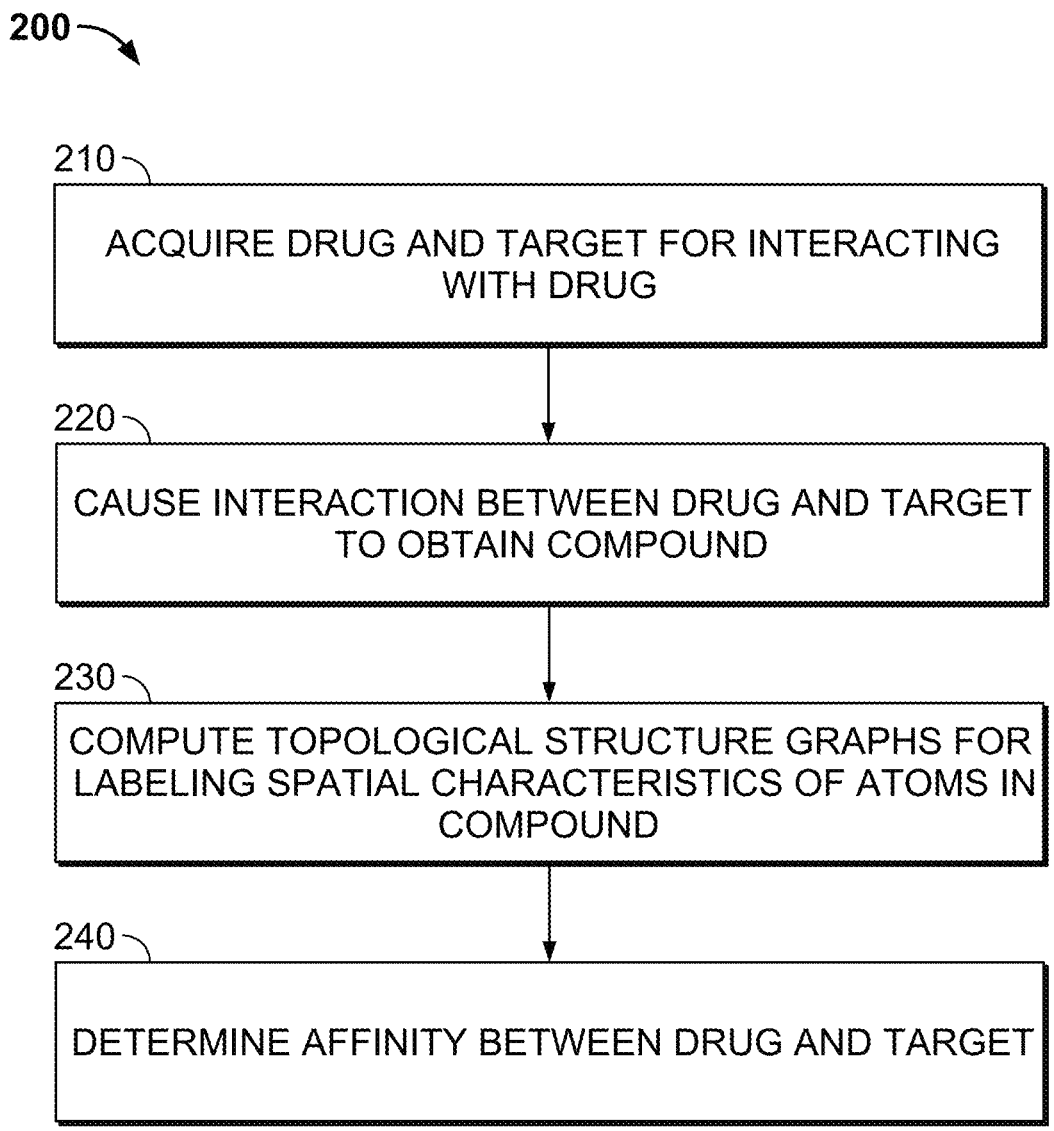
FIG. 2 is a flowchart of an embodiment of a process for predicting an affinity between a drug and a target.

FIG. 2 is a flowchart of an embodiment of a process for predicting an affinity between a drug and a target. In some embodiments, the process 200 is performed by system 1600 of FIG. 16 and comprises:

In 210, the system acquires a drug and a target for interacting with the drug.

As an example, the target is a protein pocket.

In 220, the system causes an interaction between e drug and the target to obtain a compound.

In 230, the system computes topological structure graphs for labeling spatial characteristics of atoms in the compound.

In 240, the system determines an affinity between the drug and the target based on the topological structure graphs.

In some embodiments, the affinity quantifies the extent of target-drug binding.

In operation 210, the drug can be a drug for affinity detection. The target can interact with the drug and thus can generate a compound for performing an affinity prediction operation. There are no restrictions on the manner in which the drug and the target are acquired. A person of ordinary skill in the art can implement settings based on specific application scenarios and application requirements, e.g., by presetting multiple pieces of drug data and target data. In some embodiments, the settings are related to input data. A detection module can be configured to acquire an execution operation input by a user targeting any one piece of drug data or any one piece of target data, and the obtained execution operation can determine the drug for affinity detection and the target that interacts with the drug. In some embodiments, the drug for an affinity detection operation and the target that interacts with the drug can be stored in a preset area. The drug and the target that interacts with the drug can be acquired by accessing the preset area. In some embodiments, the drug for an affinity detection operation and the target that interacts with the drug can be sent to the prediction system by a third device, thus enabling the prediction system to acquire the drug for an affinity detection operation and the target that interacts with the drug.

A person of ordinary skill in the art can adopt other approaches to acquire a drug and a target for interacting with the drug. The acquisition technique will not be further discussed for conciseness.

In 220, after the drug and the target are acquired, the system causes an interaction of the drug and the target to obtain the compound. In some embodiments, the causing of the drug-target interaction comprises: causing the drug to interact with the target, obtaining an action intensity of the interaction between the drug and the target; and in the event that the action intensity is greater than or equal to a preset threshold value, obtaining the compound that follows the drug-target interaction.

In some embodiments, after the drug and target are acquired, the interaction between the drug and the target can be caused to acquire an action intensity between the drug and the target. Please note that, in the event that interactions occur between different drugs and different targets, or the same drug interacts with different targets, the corresponding action intensities can differ. For example, in the event that an interaction occurs between Drug A and Target a, an action intensity is A-a. In the event that an interaction occurs between Drug A and Target b, an action intensity is A-b. In the event that an interaction occurs between Drug B and Target a, an action intensity is B-a. The action intensity A-a, the action intensity A-b, and the action intensity B-a can be the same or different.

Implementation of the determination of the compound that follows from drug-target interaction is not restricted. A person of ordinary skill in the art can implement settings based on specific application scenarios and application requirements, e.g., the compound can be a predicted structure obtained through a virtual docking operation or a structure obtained through detection experiments. In this example, the settings are related to compound structure prediction techniques. Typically, in the event that the compound structure is obtained through detection experiments, an instantly stable compound can be detected, but the predicted structure obtained through virtual docking is typically a virtual structure, which can be used for target discovery.

In 230, after the compound is obtained, the compound can undergo analysis and identification to compute topological structure graphs of spatial characteristics of atoms in the compound. The topological structure graphs can include at least one group. In other words, the topological structure graphs can include one or more groups. Each group of topological structure graphs can include multiple topological structure graphs, and different groups of topological structure graphs can include different numbers of topological structure graphs. In addition, the topological structure graphs can include at least one of the following: a persistent spectral graph, a persistent spectral simplicial complex, change features of the persistent spectral simplicial complex, and/or a persistent spectral hypergraph. In some embodiments, the persistent spectral graph is used to label the persistence and extent of change of topological features, and the persistent spectral hypergraph is used to label a persistence and an extent of change of topological features of a hypergraph. A topological structure graph can include more than the technical features defined above. A person of ordinary skill in the art can also implement settings based on specific application scenarios and application requirements. For example, the topological structure graph includes the persistent topological features of simplices, and these persistent topological features of simplices include: persistent topological node features, persistent topological edge features, etc.

As an example, in the event that topological structure graphs include persistent spectral graphs and persistent spectral simplicial complexes, the topological structure graphs include multiple persistent spectral graphs, and each persistent spectral graph includes one or more persistent spectral simplicial complexes, i.e., the topological structure graphs exhibit a nested structure.

In 240, after the topological structure graphs are acquired, the topological structure graphs can be analytically processed to determine the affinity between the drug and the target. As an example, the acquired topological structure graphs include at least one group. In other words, the topological structure graphs include one or more groups. In some embodiments, each group of topological structure graphs includes multiple topological structure graphs. For example, after a drug is acquired, two groups of topological structure graphs corresponding to the drug are computed. In some embodiments, one group of topological structure graphs includes 36 topological structure graphs, and the other group of topological structure graphs includes 50 topological structure graphs.

In this example, determining the affinity between the drug and the target based on the topological structure graphs includes: analytically processing each group of topological structure graphs based on a deep learning model; obtaining at least one affinity corresponding to at least one group of topological structure graphs, wherein the deep learning model is trained to determine affinities between drugs and targets based on the topological structure graphs; and determining a target affinity between the drug and the target based on the at least one affinity.

As an example, the deep learning model is pretrained to determine affinities between drugs and targets based on the topological structure graphs. After at least one group of topological structure graphs is obtained, the at least one group of topological structure graphs can be input into the deep learning model. In some embodiments, the topological structure graphs are grouped according to different binding situation. The deep learning model can analytically process each group of the topological structure graphs and thus acquire at least one affinity corresponding to the at least one group of topological structure graphs. After the at least one affinity is acquired, the at least one affinity can undergo analytical processing. In some embodiments, the at least one affinity undergoing analytical processing can include the at least one affinity undergoing processing to calculate a weighted sum of the at least one affinity. Thus, the target affinity of the target and drug can be determined.

A person of ordinary skill in the art can perform other techniques to determine the affinity between a drug and a target. The other techniques will not be further discussed for conciseness.

The process for predicting an affinity between a drug and a target can comprise: acquiring a drug and a target for interacting with the drug, causing a drug-target interaction to determine a compound, computing topological structure graphs for labeling spatial characteristics of atoms in the compound, and determining an affinity between the drug and the target based on the topological structure graphs. The process implements the determination of drug-target affinity that can be based on the topological structure graphs corresponding to the compound. The process can determine the affinity accurately and reliably, but also the process can determine the stability of drug-target action based on the predicted affinity and thus increase the utility of the prediction process.

Figure 3:
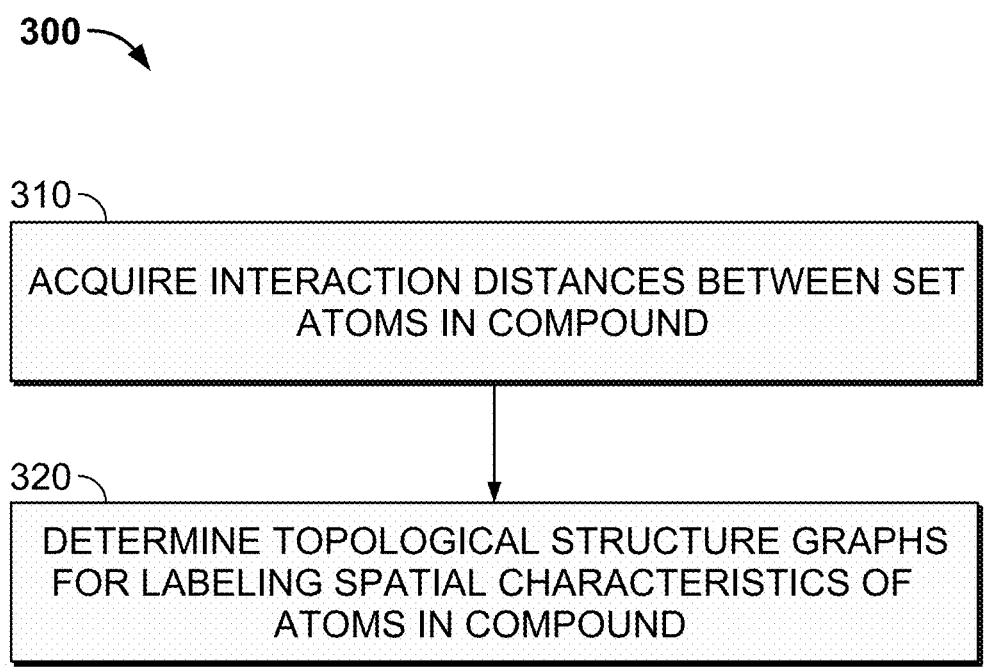
FIG. 3 is a flowchart of an embodiment of a process for computing topological structure graphs for labeling spatial characteristics of atoms in a compound.

FIG. 3 is a flowchart of an embodiment of a process for computing topological structure graphs for labeling spatial characteristics of atoms in a compound. In some embodiments, the process 300 is an implementation of operation 230 of FIG. 2 and comprises:

In 310, the system acquires interaction distances between set atoms in the compound.

In 320, the system determines topological structure graphs for labeling spatial characteristics of atoms in the compound based on the interaction distances.

In the obtaining of the compound, certain atoms in the drug can interact with certain atoms in the target. Interaction distances between atoms in the drug and target atoms at this time are to exist. In some embodiments, when the distance between atoms is small enough, there are forces between the atoms. As an example, the set atoms include at least one of the following: hydrogen atoms (H), carbon atoms (C), nitrogen atoms (N), oxygen atoms (O), and/or sulfur atoms (S) located in the drug, and hydrogen atoms (H), carbon atoms (C), nitrogen atoms (N), oxygen atoms (O), sulfur atoms (S), phosphorus atoms (P), fluorine atoms (F), chlorine atoms (Cl), bromine atoms (Br), and/or iodine atoms (I) in the target. In some embodiments, the set atoms refer to the atoms in a binding pocket, or those atoms within interaction distances. After determining the set atoms in the compound, the interaction distances between the set atoms in the compound can be acquired, e.g., the interaction distances between carbon atoms and hydrogen atoms, the interaction distances between carbon atoms and carbon atoms, the interaction distances between carbon atoms and oxygen atoms, etc.

After the interaction distances are acquired, topological structure graphs for labeling spatial characteristics of atoms in the compound can be determined to analytically process the interaction distances. In some embodiments, determining topological structure graphs for labeling spatial characteristics of atoms in the compound based on the interaction distances includes: acquiring combinatorial Laplacian matrices for labeling spatial characteristics of atoms in the compound based on the interaction distances; and determining the topological structure graphs based on the combinatorial Laplacian matrices.

As an aspect, after the interaction distances are acquired, the interaction distances can be analytically processed to acquire combinatorial Laplacian matrices for labeling spatial characteristics of atoms in the compound. As an example, the combinatorial Laplacian matrices are expressed as the following equation:

$$L_K(i, j) = \begin{cases} d(\sigma_i^k) + k + 1, & \text{if } i = j \\ 1, & \text{if } i \neq j, \ \sigma_i^k \simeq \sigma_j^k, \ \sigma_i^k \cup \sigma_j^k \text{ and } \sigma_i^k \sim \sigma_j^k \\ -1, & \text{if } i \neq j, \ \sigma_i^k \neq \sigma_j^k, \ \sigma_i^k \cup \sigma_j^k \text{ and } \sigma_i^k \not\sim \sigma_j^k \\ 0, & \text{if } i = j, \ \sigma_i^k \cong \sigma_j^k, \text{ or } \sigma_i^k \not\cong \sigma_j^k \end{cases}$$

In some embodiments, $\sigma_i^k$ represents one face. $d(\sigma_i^k)$ is used to label the level of the $\sigma_i^k$ k-simplex; $d(\sigma_i^k)$ can be the number of k+1 simplices. $\sigma_i^k \simeq \sigma_j^k$ represents the upper adjacency of two simplices. $\sigma_i^k$ and $\sigma_j^k$ have a common k+1 simplex as their face. The represented contents of and $\sigma_i^k \not\simeq \sigma_j^k$ and $\sigma_i^k \simeq \sigma_j^k$ are opposites. $\sigma_i^k \cong \sigma_j^k$ represents the lower adjacency of two simplices. $\sigma_i^k$ and $\sigma_j^k$ have a common k−1 simplex as their face. The meanings represented by $\sigma_i^k \not\cong \sigma_j^k$ and the above symbol $\sigma_i^k \cong \sigma_j^k$ are opposites. $\sigma_i^k \sim \sigma_j^k$ is used to label the fact that two simplexes have the same orientation. The meanings represented by $\sigma_i^k \not\sim \sigma_j^k$ and the above symbol $\sigma_i^k \sim \sigma_j^k$ are opposites.

After the combinatorial Laplacian matrices are acquired, the topological structure graphs for labeling spatial characteristics of atoms in the compound can be determined by analytically processing the combinatorial Laplacian matrices. This processing allows for the accurate and reliable acquisition of the topological structure graphs.

Figure 4:
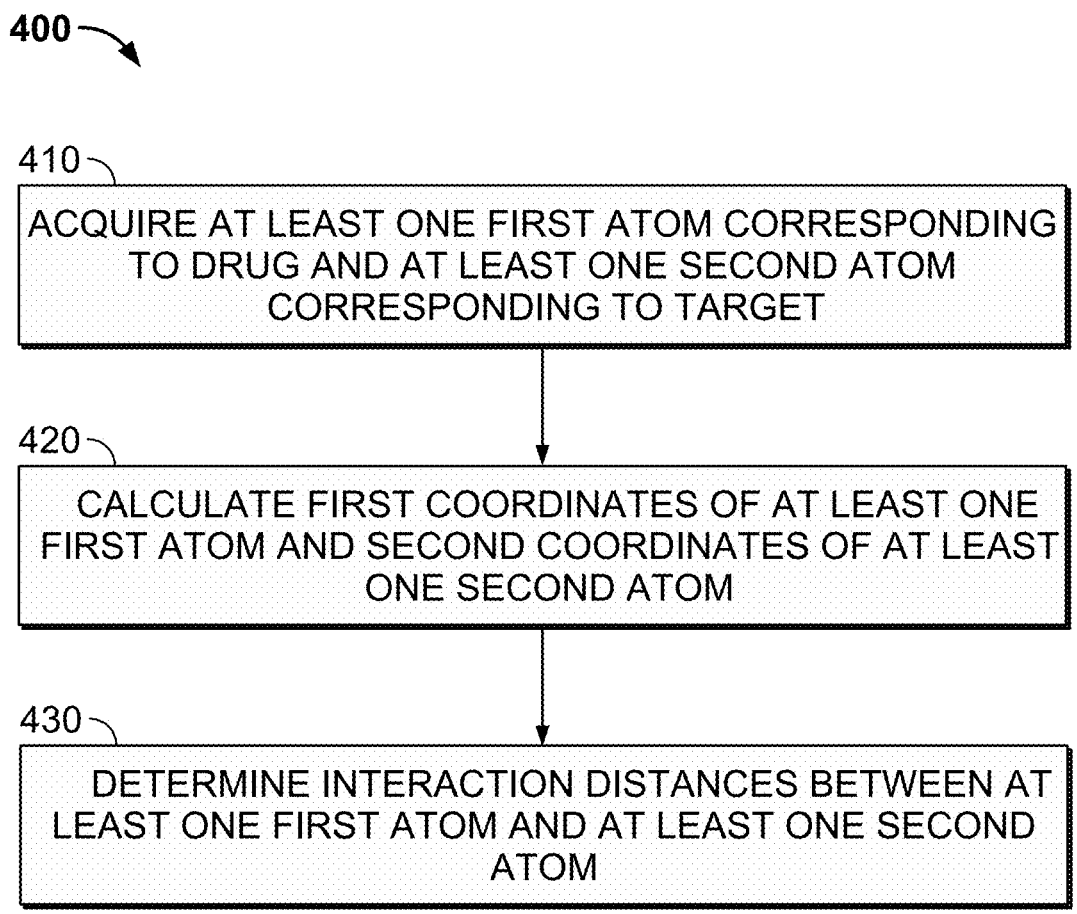
FIG. 4 is a flowchart of an embodiment of a process for acquiring interaction distances between set atoms in a compound.

FIG. 4 is a flowchart of an embodiment of a process for acquiring interaction distances between set atoms in a compound. In some embodiments, process 400 is an implementation of operation 310 of FIG. 3 and comprises:

In 410, the system chooses at least one first atom corresponding to a drug and at least one second atom corresponding to a target.

In 420, the system calculates first coordinates of the at least one first atom and second coordinates of the at least one second atom.

In 430, the system determines interaction distances between the at least one first atom and the at least one second atom based on the first coordinates and the second coordinates.

The at least one first atom corresponding to the drug can include at least one of the following: carbon atom (C), nitrogen atom (N), oxygen atom (O), and/or sulfur atom (S). The at least one second atom corresponding to the target can include at least one of the following: carbon atom (C), nitrogen atom (N), oxygen atom (O), sulfur atom (S), phosphorus atom (P), fluorine atom (F), chlorine atom (Cl), bromine atom (Br), and/or iodine atom (I).

To accurately acquire the interaction distances between set atoms in the compound in the event that the drug is interacting with the target, at least one first atom corresponding to the drug and at least one second atom corresponding to the target can be acquired. Then the first coordinates of the at least one first atom and second coordinates of the at least one second atom are calculated. After the first coordinates and the second coordinates are acquired, the first coordinates and the second coordinates can undergo analytical processing to determine the interaction distances between the at least one first atom and the at least one second atom.

In some embodiments, determining the interaction distances between the at least one first atom and the at least one second atom based on the first coordinates and second coordinates includes: determining Euclidean distances between the at least one first atom and the at least one second atom based on the first coordinates and second coordinates; and determining the Euclidean distances to correspond to the interaction distances between the at least one first atom and the at least one second atom.

As an example, after the first coordinates and the second coordinates are acquired, the first coordinates and the second coordinates can undergo analytical processing to determine the Euclidean distance between the at least one first atom and the at least one second atom. The Euclidean distance can be expressed using the following formula:

$$M(m_i, m_j) = \begin{cases} \|r_j - r_j\|, & \text{if } r_i \in R_P, r_j \in R_L \text{ or } r_i \in R_L, r_j \in R_P; \\ \infty, & \text{Otherwise.} \end{cases}$$

In some embodiments, $r_i$ is the first coordinate of a first atom, $r_j$ is the second coordinate of a second atom, and $M(m_i, m_j)$ is the Euclidean distance. After the Euclidean distances are acquired, the Euclidean distances can be determined as the interaction distances between the at least one first atom and the at least one second atom.

As an example, the number of the at least one first atom corresponding to the drug is 4 and the number of the at least one second atom corresponding to the target is 9. Therefore, in the example, the number of interaction distances between the first atoms and the second atoms is 36.

In some embodiments, the at least one first atom corresponding to the drug and the at least one second atom corresponding to the target are acquired; the first coordinates of the at least one first atom and the second coordinates of the at least one second atom are calculated; and the interaction distances between the at least one first atom and the at least one second atom are determined based on the first coordinates and the second coordinates. This not only provides a way to determine the interaction distance, but also provides an accurate and reliable determination of the interaction distance.

Figure 5:
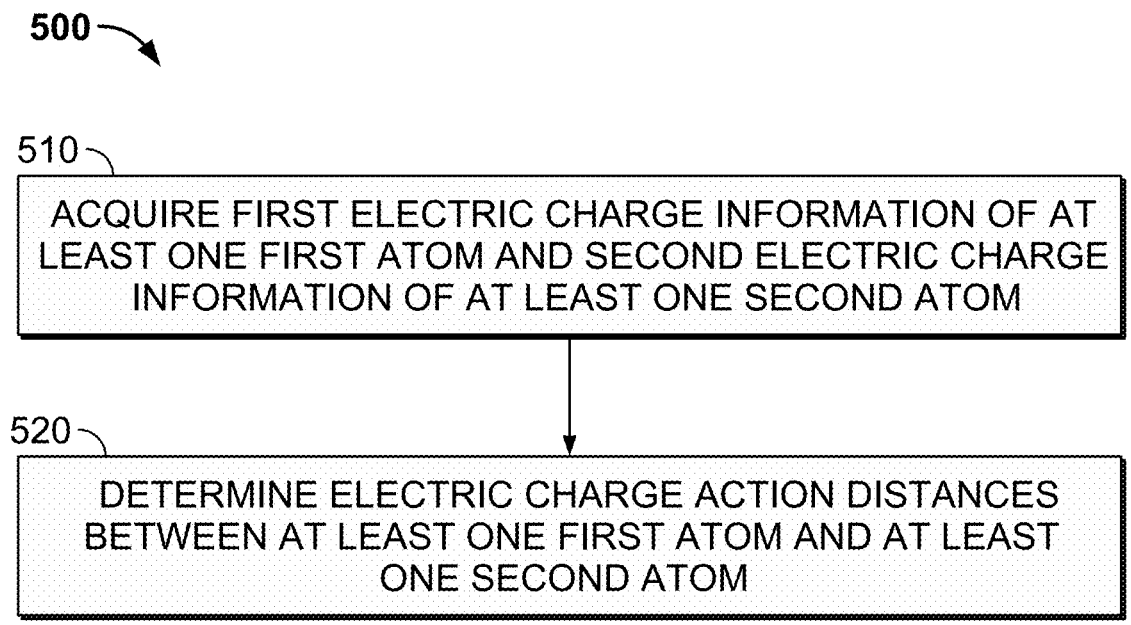
FIG. 5 is a flowchart of an embodiment of a process for determining interaction distances between at least one first atom and at least one second atom based on first coordinates and second coordinates.

FIG. 5 is a flowchart of an embodiment of a process for determining interaction distances between at least one first atom and at least one second atom based on first coordinates and second coordinates. In some embodiments, process 500 is an implementation of operation 430 of FIG. 4 and comprises:

In 510, the system acquires first electric charge information of the at least one first atom and second electric charge information of the at least one second atom.

In 520, the system determines electric charge action distances between the at least one first atom and the at least one second atom based on the first coordinates, the second coordinates, the first electric charge information, and the second electric charge information.

After determining the interaction distances of the at least one first atom and the at least one second atom, the first electric charge information of the at least one first atom and the second electric charge information of the at least one second atom can be acquired. As an example, in the event that the drug and the target are interacting, physical features and chemical features of the first atoms and the second atoms can be determined and first electric charge information of the first atoms and second electric charge information of the second atoms can be determined based on the physical features and the chemical features of the first atoms and the second atoms. A person of ordinary skill in the art can adopt other approaches to acquire the first electric charge information of the first atom and the second electric charge information of the second atom.

After the first electric charge information of the at least one first atom and the second electric charge information of the at least one second atom are acquired, the first coordinates, the second coordinates, the first electric charge information, and the second electric charge information can be analytically processed to determine electric charge action distances between the at least one first atom and the at least one second atom. In some embodiments, determining the electric charge action distances between the at least one first atom and the at least one second atom based on the first coordinates, the second coordinates, the first electric charge information, and the second electric charge information includes: determining Euclidean distances between the at least one first atom and the at least one second atom based on the first coordinates and the second coordinates; and determining the electric charge action distances between the at least one first atom and the at least one second atom based on the Euclidean distances, the first electric charge information, and the second electric charge information.

As an example, after the first coordinates and the second coordinates are acquired, the first coordinates and the second coordinates undergo analytical processing to determine the Euclidean distances between the at least one first atom and the at least one second atom. The Euclidean distances, the first electric charge information, and the second electric charge information can be analytically processed to determine the electric charge action distances between the at least one first atom and the at least one second atom. As an aspect, an electric charge action distance can be expressed using the formula below:

$$M_E(m_i, m_j) = \begin{cases} \dfrac{1}{1 + \exp\left(\dfrac{cq_i q_j}{\|r_i - r_j\|}\right)}, & \text{if } r_i \in R_P, r_j \in R_L \text{ or } r_i \in R_L, r_j \in R_P; \\ \infty, & \text{Otherwise.} \end{cases}$$

In some embodiments, $M_E(m_i, m_j)$ are the electric charge action distances; $q_i$ is used to label the first electric charge information of the first atoms, and $q_j$ is used to label the second electric charge information of the second atoms; $r_i$ is used to label the first coordinates of the first atoms, and $r_j$ is used to label the second coordinates of the second atoms; and c is the setting parameter. As obtained through the above formula, an electric charge action distance can be positively related to the first electric charge information, an electric charge action distance can be positively related to the second electric charge information, and an electric charge action distance can be negatively related to the Euclidean distance.

As an example, the number of the at least one first atom corresponding to the drug is 5 and the number of the at least one second atom corresponding to the target is 10. Therefore, in the example, the number of electric charge action distances between the first atoms and the second atoms is 50.

In some embodiments, after the first electric charge information of the at least one first atom and the second electric charge information of the at least one second atom are acquired, the electric charge action distances between the at least one first atom and the at least one second atom are determined based on the first coordinates, the second coordinates, the first electric charge information, and the second electric charge information. This approach provides another way to determine the interaction distances, and also ensures an accurate and reliable determination of the interaction distances.

Figure 6A:
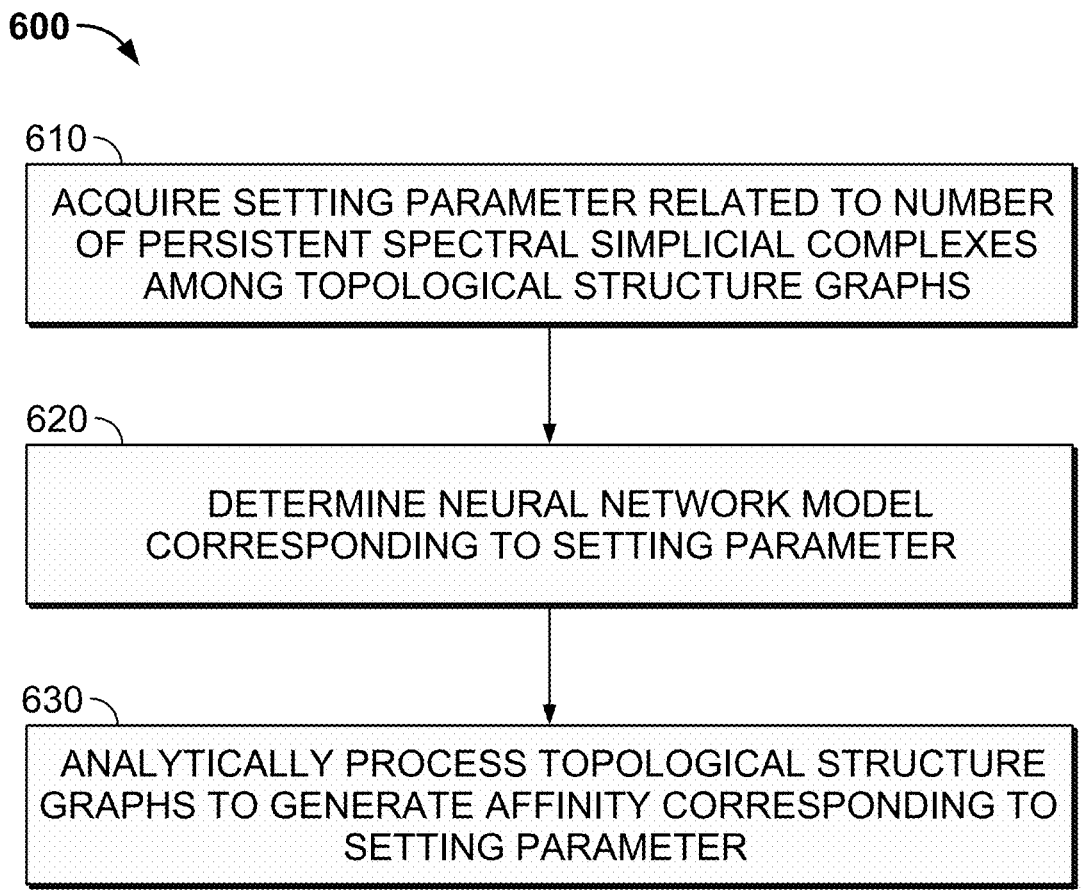
FIG. 6A is a flowchart of an embodiment of a process for determining an affinity between a drug and a target based on topological structure graphs.

FIG. 6A is a flowchart of an embodiment of a process for determining an affinity between a drug and a target based on topological structure graphs. In some embodiments, process 600 is an implementation of operation 240 of FIG. 2 and comprises:

In 610, the system acquires a setting parameter related to a number of persistent spectral simplicial complexes among topological structure graphs.

In 620, the system determines a neural network model corresponding to the setting parameter.

In 630, the system analytically processes the topological structure graphs to generate an affinity corresponding to the setting parameter based on the neural network model.

In the event, that the topological structure graphs include persistent spectral simplicial complexes, the number of persistent spectral simplicial complexes can be related to a setting parameter β, and different setting parameters can correspond to different neural network models. After the topological structure graphs are acquired, the number of persistent spectral simplicial complexes included in the topological structure graphs can be counted. After the number of persistent spectral simplicial complexes has been counted, the setting parameter can be acquired based on the number of persistent spectral simplicial complexes. For example, the setting parameter β is 0 or 1. A person of ordinary skill in the art can set the setting parameter β to another argument based on a specific application scenario or an application requirement. For example, the setting parameter β can be 2, 3, 4, or another value.

Since different setting parameters can correspond to different neural network models, after the setting parameter is acquired, the neural network corresponding to the setting parameter can be determined. As an example, determining the neural network model corresponding to the setting parameter includes: in the event that the setting parameter is 0, determining that the neural network model is a first subnetwork model for determining a one-dimensional affinity between the drug and the target; and in the event that the setting parameter is 1, determining that the neural network model is a second subnetwork model for determining a two-dimensional affinity between the drug and the target.

After the neural network model is determined, the topological structure graphs can be analytically processed based on the neural network model, and thus an affinity corresponding to the setting parameter can be generated. As an example, analytically processing the topological structure graph to generate an affinity corresponding to the setting parameter based on the neural network model includes: in the event that the neural network model is a first subnetwork model, analytically processing the topological structure graphs to determine the one-dimensional affinity corresponding to the setting parameter based on the first subnetwork model; and in the event that the neural network model is a second subnetwork model, analytically processing the topological structure graphs to determine the two-dimensional affinity corresponding to the setting parameter based on the second subnetwork model.

In an example, in the event that different neural network models are determined based on different setting parameter values, the topological structure graphs to be analytical processed by a neural network model can be acquired in different ways. As an example, in the event that the setting parameter is 0, the obtained topological structure graphs are first topological structure graphs, obtained through computational processing, that are for labeling spatial characteristics of atoms in a compound; and in the event that the setting parameter is 1, the obtained topological structure graphs are second topological structure graphs, obtained through computational processing, that are for labeling spatial characteristics of atoms in a compound. The number of second topological structure graphs can be more than one and can correspond to multiple different observation parameters.

In another example, computing second topological structure graphs for labeling spatial characteristics of atoms in a compound includes: acquiring multiple different observation parameters, and determining multiple second topological structure graphs based on the multiple different observation parameters. For example, the multiple different observation parameters include $\eta_1$, $\eta_2$, $\eta_3$, and $\eta_4$-four observation parameters that can correspond to different observation angles. After multiple different observation parameters are acquired, second topological structure graphs corresponding to these Observation parameters can be determined. The topological structure graphs corresponding to the different observation parameters can be represented in different forms.

On the other hand, in the event that the first subnetwork model is used to analytically process the topological structure graphs, the topological structure graphs include: first topological structure graphs determined by Euclidian distances between atoms and second topological structure graphs determined by electric charge action distances. Therefore, a one-dimensional affinity can be acquired by analytically processing the first topological structure graphs based on the first subnetwork model; another one-dimensional affinity can be acquired by analytically processing the second topological structure graphs based on the first subnetwork model; a two-dimensional affinity can be acquired by analytically processing the first topological structure graphs based on the second subnetwork model; and another two-dimensional affinity can be acquired by analytically processing the second topological structure graphs based on the second subnetwork model. At this point, the number of affinities obtained can be four.

In some embodiments, after the setting parameter related to the number of persistent spectral simplicial complexes in the topological structure graphs is acquired, the neural network model corresponding to the setting parameter is determined, and the neural network model is used to analytically process the topological structure graphs. The affinities corresponding to the setting parameter can be generated in a stable and effective manner.

Figure 6B:
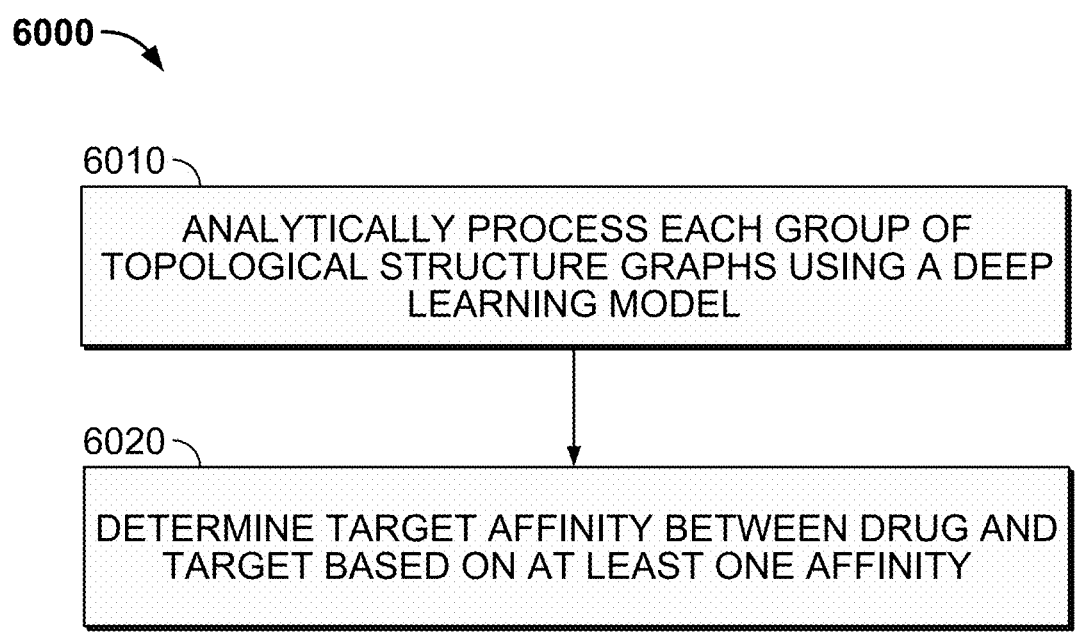
FIG. 6B is a flowchart of another embodiment of a process for determining an affinity between a drug and a target based on topological structure graphs.

FIG. 6B is a flowchart of another embodiment of a process for determining an affinity between a drug and a target based on topological structure graphs. In some embodiments, process 6000 is an implementation of operation 240 of FIG. 2 and comprises:

In 6010, the system analytically processes each group of topological structure graphs using a deep learning model to obtain at least one affinity corresponding to at least one group of the topological structure graphs.

In some embodiments, the deep learning model is trained to determine affinities between drugs and targets based on the topological structure graphs.

In 6020, the system determines a target affinity between a drug and a target based on the at least one affinity.

Figure 7:
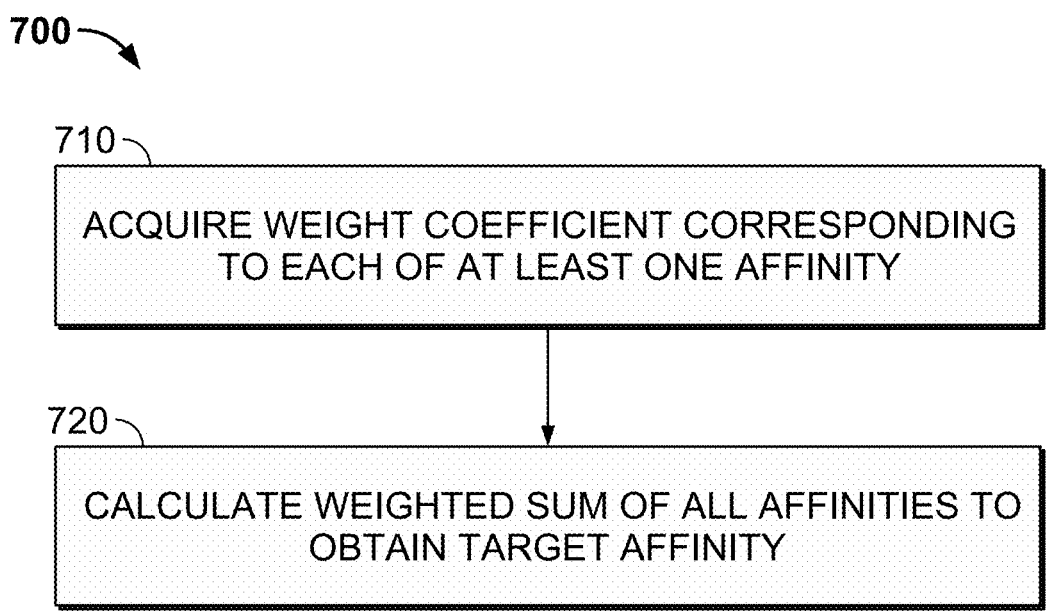
FIG. 7 is a flowchart of an embodiment of a process for determining a target affinity between a drug and a target based on at least one affinity.

Since more than one affinity can be acquired, multiple affinities can be analytically processed following the acquisition of multiple affinities to determine a target affinity. FIG. 7 is a flowchart of an embodiment of a process for determining a target affinity between a drug and a target based on at least one affinity. In some embodiments, process 700 is an implementation of operation 6020 of FIG. 6B and comprises:

In 710, the system acquires a weight coefficient corresponding to each of at least one affinity.

In 720, the system calculates, based on the weight coefficients, a weighted sum of all affinities to obtain the target affinity between the drug and the target.

After at least one affinity is acquired, weight coefficients corresponding to each affinity can be acquired and then the weighted sum of all the affinities can be calculated based on the weight coefficients to obtain the target affinity between the drug and the target. As an example, the at least one affinity includes $Y_1$, $Y_2$, $Y_3$, and $Y_4$. The weight coefficient $p_1$ corresponding to $Y_1$, the weight coefficient $p_2$ corresponding to $Y_2$, the weight coefficient $p_3$ corresponding to $Y_3$, and the weight coefficient $p_4$ corresponding to $Y_4$ can be obtained. After the weight coefficients are acquired, the following formula can be used to determine the target affinity: $Y_c = p_1*Y_1 + p_2*Y_2 + p_3*Y_3 + p_4*Y_4$, thus an accurate and reliable determination of the target affinity can be ensured.

Figure 8:
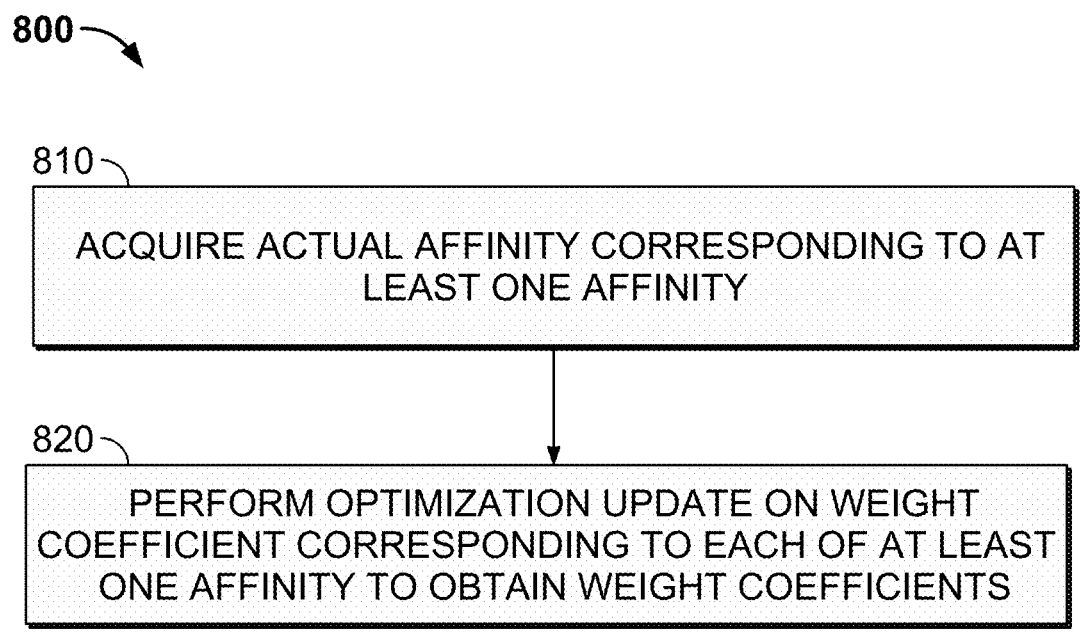
FIG. 8 is a flowchart of an embodiment of a process for acquiring a weight coefficient corresponding to each of at least one affinity.

FIG. 8 is a flowchart of an embodiment of a process for acquiring a weight coefficient corresponding to each of at least one affinity. In some embodiments, process 800 is an implementation of operation 710 of FIG. 7 and comprises:

In 810, the system acquires an actual affinity corresponding to at least one affinity.

In 820, the system performs, based on the actual affinity and the at least one affinity, an optimization update on the weight coefficient corresponding to each of the at least one affinity to obtain weight coefficients.

To increase the accuracy of predicting the target affinity after the weight coefficient corresponding to each affinity is acquired, an actual affinity corresponding to the at least one affinity can be acquired to perform processing on weight coefficients based on the actual affinity and the at least one affinity to obtain the weight coefficients.

In an example, using the actual affinity and at least one affinity to perform an optimization update on the weight coefficient corresponding to each of the at least one affinity to obtain updated weight coefficients includes: acquiring correlation coefficients between at least two affinities and the actual affinity, and using an optimization function to perform maximization processing on the correlation coefficients to obtain an updated weight coefficient corresponding to each affinity.

After the at least one affinity is acquired, the correlation coefficients between the at least two affinities and the actual affinity can be acquired. As an example, Pearson correlation coefficients between the at least two affinities and the actual affinity are acquired. After the Pearson correlation coefficients are acquired, an optimization function can be used to perform maximization processing on the correlation coefficients to obtain a weight coefficient corresponding to each affinity.

As an example, the at least one affinity includes $Y_1$, $Y_2$, $Y_3$, and $Y_4$, and the actual affinity is $Y_G$; the subsequently acquired initial weight coefficients corresponding to the affinities include: $a_0$, $b_0$, $c_0$, $d_0$, $p_0$, and $q_0$; and intermediate affinities corresponding to the at least one affinity can be acquired: $Y_{c1} = a_0 Y_1 + b_0 Y_2$, $Y_{c2} = c_0 Y_3 + d_0 Y_4$, $Y_c = p_0 Y_{c1} + q_0 Y_{c2}$. After the intermediate affinities are acquired, the Pearson coefficients between the intermediate affinities and the actual affinity can be determined, i.e., $Cor(Y_{c1}, Y_G)$, $Cor(Y_{c2}, Y_G)$ and $Cor(Y_c, Y_G)$.

After the Pearson coefficients are acquired, the optimization technique Opt=Nelder-Mead can be used to perform optimization processing on the Pearson coefficients to obtain weight coefficients. The formulas can include:

$a_0$, $b_0 \leftarrow Opt(max(Cor(Y_{c1}, Y_G)))$, i.e., by using this formula, optimization processing can be performed on $a_0$ and $b_0$, thus to obtain the weight coefficients $a_1$ and $b_1$;

$c_0$, $d_0 \leftarrow Opt(max(Cor(Y_{c2}, Y_G)))$, i.e., by using this formula, optimization processing can be performed on $c_0$ and $d_0$, thus to obtain the weight coefficients $c_1$ and $d_1$;

$p_0$, $q_0 \leftarrow Opt(max(Cor(Y_c, Y_G)))$, i.e., by using this formula, optimization processing can be performed on $p_0$ and $q_0$, thus to obtain the weight coefficients $p_1$ and $q_1$.

After the weight coefficients are acquired, the optimized weight coefficients can be stored in a preset area. The weight coefficient corresponding to each affinity can be acquired upon accessing the preset area, and then the at least one affinity can undergo analytical processing using the processed weight coefficients to determine the target affinity between the drug and the target. This processing can effectively make the determination of affinities more accurate and reliable.

Figure 9:
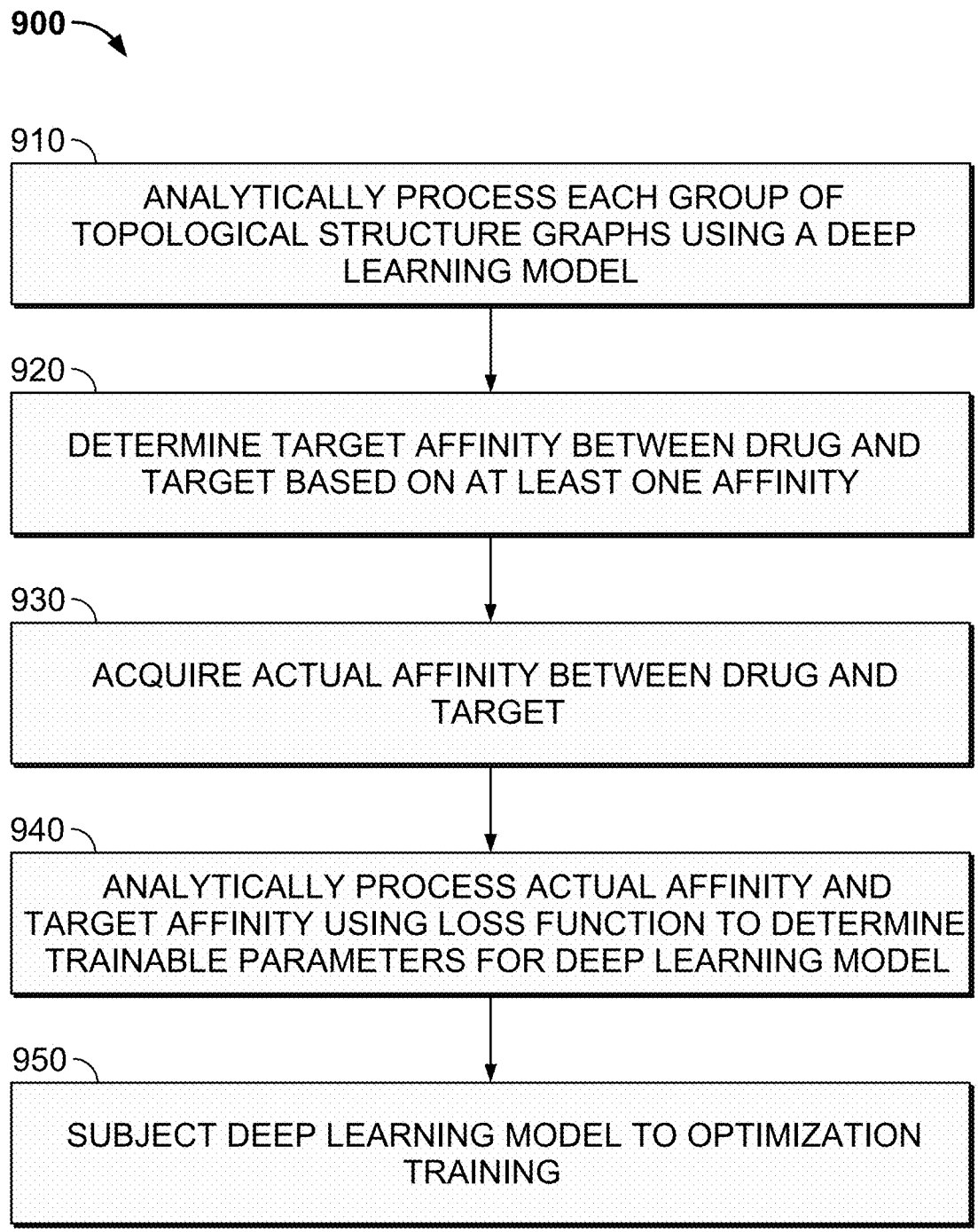
FIG. 9 is a flowchart of yet another embodiment of a process for determining an affinity between a drug and a target based on topological structure graphs.

FIG. 9 is a flowchart of yet another embodiment of a process for determining an affinity between a drug and a target based on topological structure graphs. In some embodiments, process 900 is an implementation of operation 240 of FIG. 2 and comprises:

Operations 910 and 920 of FIG. 9 correspond with operations 6010 and 6020 of FIG. 6B.

In 910, the system analytically processes each group of topological structure graphs using a deep learning model to obtain at least one affinity corresponding to at least one group of the topological structure graphs.

In some embodiments, the deep learning model is trained to determine affinities between drugs and targets based on the topological structure graphs.

In 920, the system determines a target affinity between a drug and a target based on the at least one affinity.

In 930, the system acquires an actual affinity between the drug and the target.

In 940, the system analytically processes the actual affinity and the target affinity using a loss function to determine trainable parameters for a deep learning model.

In 950, the system subjects the deep learning model to optimization training based on the trainable parameters to obtain a trained deep learning model.

To increase the prediction accuracy of the deep learning model relating to the affinity between the drug and the target, after the target affinity between the drug and the target has been acquired, the actual affinity between the drug and the target can be acquired. After the actual affinity and the target affinity have been acquired, the actual affinity and the target affinity can be analytically processed using a loss function to determine trainable parameters of the deep learning model. As an example, the following formula is used to determine the training parameters of the deep learning model: loss=L $(Y_p, Y_G)$, wherein $Y_p$ is the target affinity, $Y_G$ is the actual affinity, and L is the loss function. During a specific implementation, the loss function L can be a root mean square error (RMSE) function, and the loss parameter between the actual affinity and the target affinity can be obtained. The trainable parameters of the deep learning model can be determined using the loss parameter.

After the trainable parameters are acquired, the deep learning model can be subjected to optimization training based on the trainable parameters to obtain a trained deep learning model. The trained deep learning model is configured to perform prediction operations regarding the affinity between the drug and the target. This approach can increase the accuracy and reliability of affinity prediction.

In some embodiments, the deep learning model includes a first model for generating a one-dimensional affinity and a second model for generating a two-dimensional affinity. In this case, subjecting the deep learning model to optimization processing based on the trainable parameters to obtain a trained deep learning model can include: subjecting the first model to optimization training based on the trainable parameters to obtain a first trained model; subjecting the second model to optimization training based on the trainable parameters to obtain a second trained model; and obtaining a trained deep learning model based on the first trained model and the second trained model.

In the event that the deep learning model includes a first model and a second model, the deep learning model can undergo multi-level optimization operations to ensure the quality and effectiveness of the deep learning model optimization. As an example, trainable parameters are used to subject the first model to optimization training to obtain a first trained model, and trainable parameters are also used to subject the second model to optimization training to obtain a second trained model.

Please note that the performance sequence between the operation of "subjecting the first model to optimization training" and the operation of "subjecting the second model to optimization training" can be performed in any order. For example, the operation of "subjecting the first model to optimization training based on the trainable parameters to obtain a first trained model" and the operation of "subjecting the second model to optimization training based on the trainable parameters to obtain a second trained model" are executed simultaneously. In another example, the operation of "subjecting the first model to optimization training based on the trainable parameters to obtain a first trained model" is executed after the operation of "subjecting the second model to optimization training based on the trainable parameters to obtain a second trained model."

After the first trained model and the second trained model are acquired, the first trained model and the second trained model can be analytically processed to obtain a trained deep learning model. The quality and effectiveness of deep learning model training is thus effectively ensured.

Figure 12:
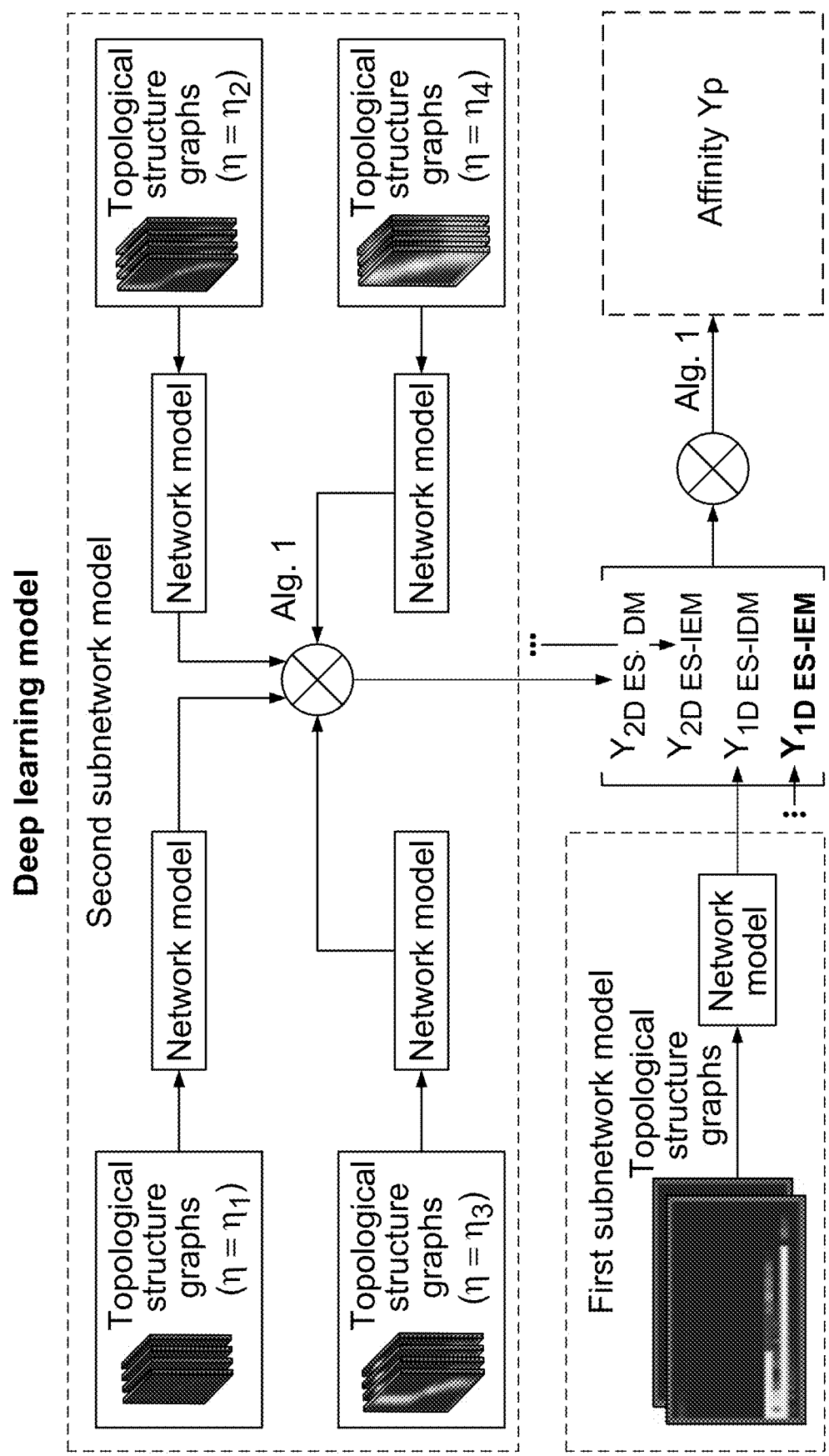
FIG. 12 is a schematic diagram of an embodiment of a process for predicting an affinity between a drug and a target.

FIG. 12 is a schematic diagram of an embodiment of a process for predicting an affinity between a drug and a target. In some embodiments, the process can perform the following operations in advance:

In operation 1, the system acquires a drug and a target for interacting with the drug.

In operation 2, the system causes an interaction between the drug and the target to determine a compound.

In operation 3, the system acquires interaction distances between set atoms in the compound.

In a first technique, the system acquires at least one first atom corresponding to the drug and at least one second atom corresponding to the target; computes first coordinates of the at least one first atom and second coordinates of the at least one second atom, and determines the Euclidean distances between the at least one first atom and the at least one second atom based on the first coordinates and the second coordinates; and determines that the Euclidean distances between the at least one first atom and the at least one second atom to be the interaction distances.

In a second technique, the system determines the Euclidean distances between the at least one first atom and the at least one second atom based on the first coordinates and the second coordinates; acquires first electric charge information of the at least one first atom and second electric charge information of the at least one second atom; and determines electric charge action distances between the at least one first atom and the at least one second atom based on the Euclidean distances, the first electric charge information, and the second electric charge information. In some embodiments, the obtained electric charge action distance is positively related to the first electric charge information, the electric charge acting distance is positively related to the second electric charge information, and the electric charge acting distance is negatively related to the Euclidean distance.

In operation 4, the system determines two groups of topological structure graphs for labeling spatial characteristics of atoms in the compound based on the interaction distances. In some embodiments, each group of topological structure graphs includes multiple topological structure graphs.

After the interaction distances are acquired, the interaction distances can be analytically processed to determine the topological structure graphs. In some embodiments, in the event that the interaction distances are Euclidean distances, a first group of topological structure graphs can be determined based on the Euclidean distances. The first group of topological structure graphs can include 36 topological structure graphs. In the event that the interaction distances are electrical charge action distances, a second group of topological structure graphs can be determined based on the electrical charge action distances. The second group of topological structure graphs can include 50 topological structure graphs.

Figure 10:
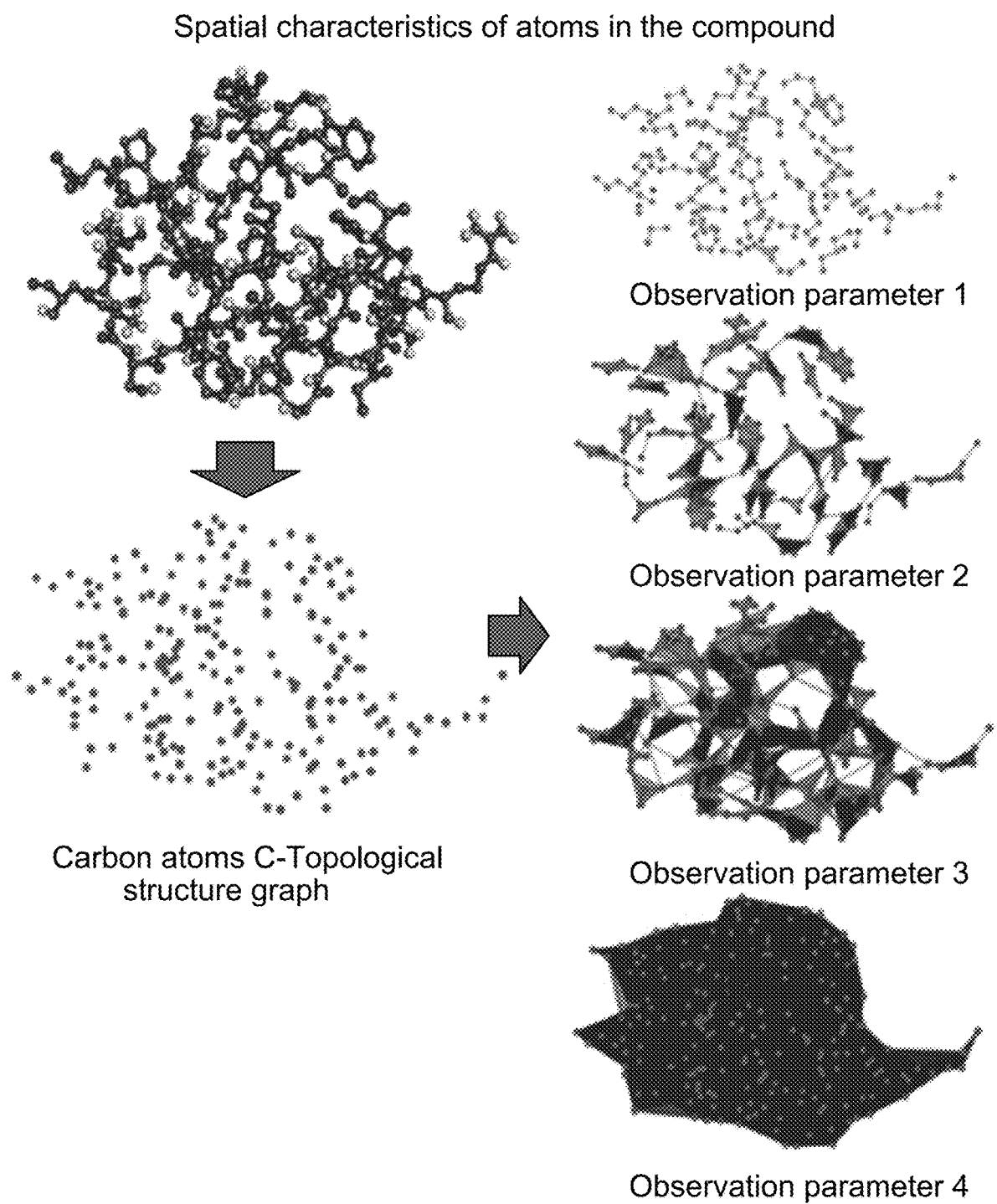
FIG. 10 is a diagram of an example of a process for determining topological structure graphs for labeling spatial characteristics of atoms in a compound.
Figure 11:
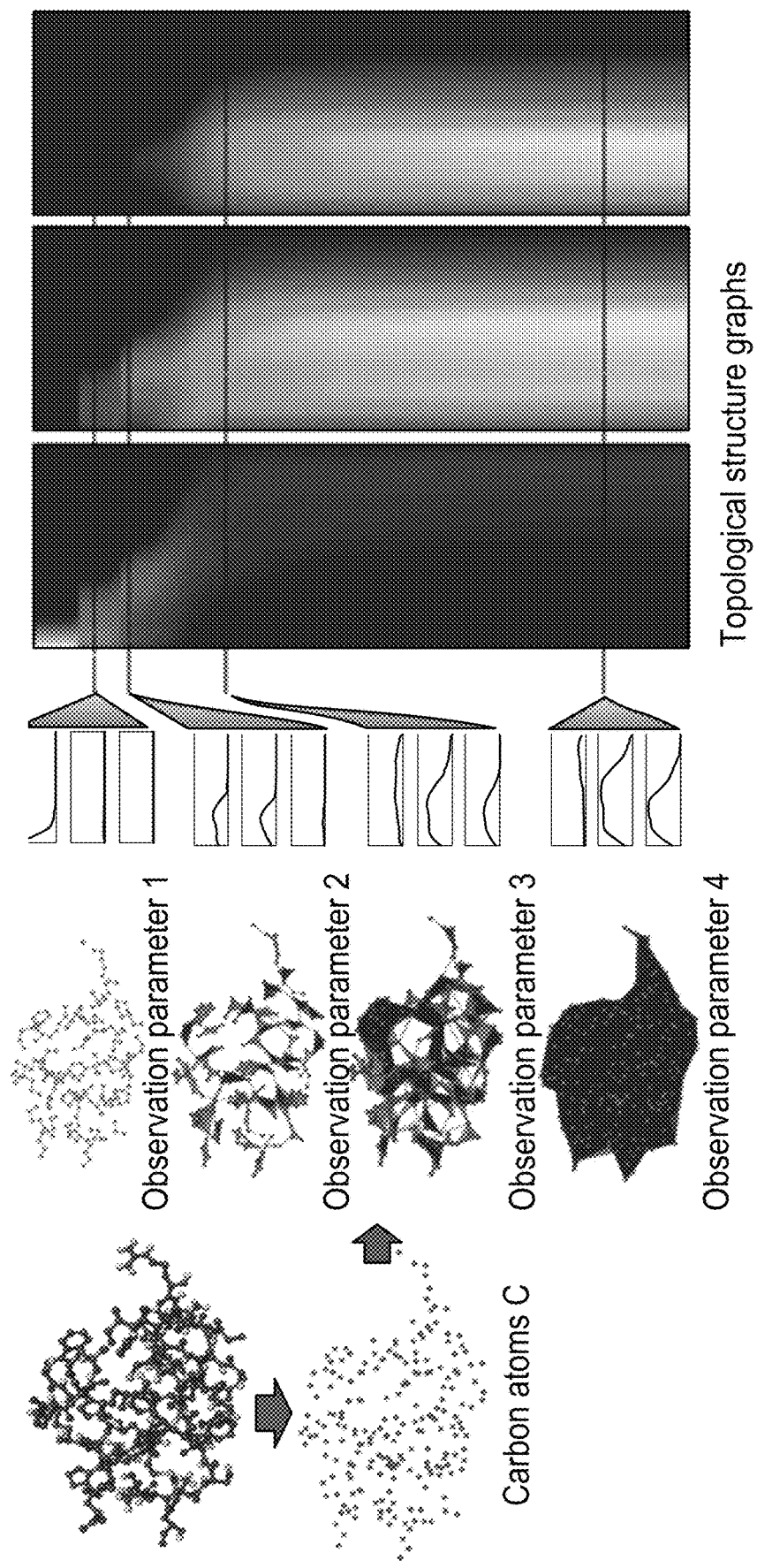
FIG. 11 is a diagram of another example of a process for determining topological structure graphs for labeling spatial characteristics of atoms in a compound.

As an example, since the set atoms in the compound include at least one of the following: carbon atoms (C), nitrogen atoms (N), oxygen atoms (O), sulfur atoms (S), phosphorous atoms (P), fluorine atoms (F), chlorine atoms (Cl), bromine atoms (Br), and/or iodine atoms (I), and different set atoms correspond to different interaction distances, the topological structure graphs corresponding to different set atoms can also vary. Using carbon atoms (C) as an example, after the compound is acquired, topological structure graphs for labeling the spatial characteristics of carbon atoms (C) in the compound can be determined. In determining the topological structure graphs, multiple different observation parameters can be acquired. For example, multiple different observation parameters include observation parameter 1, observation parameter 2, observation parameter 3, and observation parameter 4. FIG. 10 is a diagram of an example of a process for determining topological structure graphs for labeling spatial characteristics of atoms in a compound. As shown in FIG. 10, the different observation parameters can correspond to different spatial characteristics of atoms. After multiple different observation parameters are acquired, the topological structure graphs corresponding to multiple different observation parameters can be determined. FIG. 11 is a diagram of another example of a process for determining topological structure graphs for labeling spatial characteristics of atoms in a compound. In FIG. 11, in the event that the different observation parameters include $\eta_1$, $\eta_2$, $\eta_3$, and $\eta_4$, topological structure graphs corresponding to the different observation parameters can be determined.

Referring back to FIG. 12, in operation 5, the system analytically processes each topological structure graph based on the deep learning model to determine affinities corresponding to each topological structure graph.

The deep learning model can include a first subnetwork model and a second subnetwork model. The first subnetwork model can analytically process topological structure graphs to generate one-dimensional affinities. As an example, since the topological structure graphs include first-type topological structure graphs determined by Euclidean distances and second-type topological structure graphs determined by electrical charge action distances, in the event that the first subnetwork model analytically processes the topological structure graphs, the analytically processing can include: the first subnetwork model analytically processing the first-type topological structure graphs to obtain first-type one-dimensional affinities $Y_{1D\_ES\text{-}ID}$, and the first subnetwork model analytically processing the second-type topological structure graphs to obtain second-type one-dimensional affinities $Y_{1D\_ES\text{-}IEM}$.

The second subnetwork model can analytically process topological structure graphs to generate two-dimensional affinities. As an example, since the topological structure graphs include first-type topological structure graphs determined by Euclidean distances and second-type topological structure graphs determined by electrical charge action distances, in the event that the second subnetwork model analytically processes the topological structure graphs, the topological structure graphs can include: the second subnetwork model analytically processing first-type topological structure graphs to obtain first-type two-dimensional affinities $Y_{2D\_ES\text{-}IDM}$, and the second subnetwork model analytically processing second-type topological structure graphs to obtain second-type two-dimensional affinities $Y_{2D\_ES\text{-}I}$.

Please note that, in the event that the second subnetwork model is used to analytically process topological structure graphs, the topological structure graphs can also include topological structure graphs corresponding to different observation parameters. The second subnetwork model can include network models corresponding to different observation parameters. After the observation parameters are acquired, network models corresponding to the observation parameters can be used to analytically process the corresponding topological structure graphs to effectively determine two-dimensional affinities.

In operation 6, the system determines the target affinity between the drug and the target based on the affinities corresponding to each topological structure graph.

Weight coefficients corresponding to each topological structure graph are acquired, and the weighted sum of the obtained affinities can be calculated based on the weight coefficients to obtain the target affinity between the drug and the target. For example, multiple affinities include $Y_1$, $Y_2$, $Y_3$, and $Y_4$. After the multiple affinities are acquired, the following formula can be used to determine the target affinity: $Y_C = apY_1 + bpY_2 + cqY_3 + dqY_4$. The weight coefficients are ap, bp, cq, and dq, respectively.

In operation 7, the system acquires the actual affinity between the drug and the target following acquisition of the target affinity. A loss function can be used to analytically process the actual affinity and the target affinity to determine trainable parameters of the deep learning model. The deep learning model undergoes optimization training based on the trainable parameters to obtain a trained deep learning model.

After the trained deep learning model is acquired, the trained deep learning model can be used to predict the affinity between the drug and the target. This effectively ensures the accuracy and reliability of affinity prediction. As an example, in the event that the prediction process is applied to three open datasets (including PDBbind-v2007, PDBbind-v2013, and PDBbind-v2016, which are publicly available), the prediction process provides a smaller root-mean-square deviation and a closer Pearson correlation coefficient (PCC) to the true value over other conventional prediction techniques. Refer to the table below for the specific numerical values:

| Dataset | Affinity (1D) | Affinity (2D) | Affinity (1D) | Affinity (2D) | Combination |
|---|---|---|---|---|---|
| PDB-v2007 | 0.813 (1.423) | 0.823 (1.418) | 0.827 (1.395) | 0.829 (1.403) | 0.846 (1.230) |
| PDB-v2013 | 0.770 (1.508) | 0.780 (1.498) | 0.779 (1.486) | 0.784 (1.483) | 0.812 (1.422) |
| PDB-v2016 | 0.810 (1.359) | 0.825 (1.322) | 0.825 (1.324) | 0.831 (1.307) | 0.851 (1.309) |

The process for predicting the affinity between a drug and a target can comprise: acquiring a drug and a target for interacting with the drug, causing a drug-target interaction to determine the compound, computing topological structure graphs for labeling spatial characteristics of atoms in the compound, and determining an affinity between the drug and the target based on the topological structure graphs. This process can effectively implement a determination of drug-target affinity that can be based on the topological structure graphs corresponding to a compound. As a result, this prediction process determines the affinity accurately and reliably, but also helps to promote the development of the drug technology field.

Figure 13:
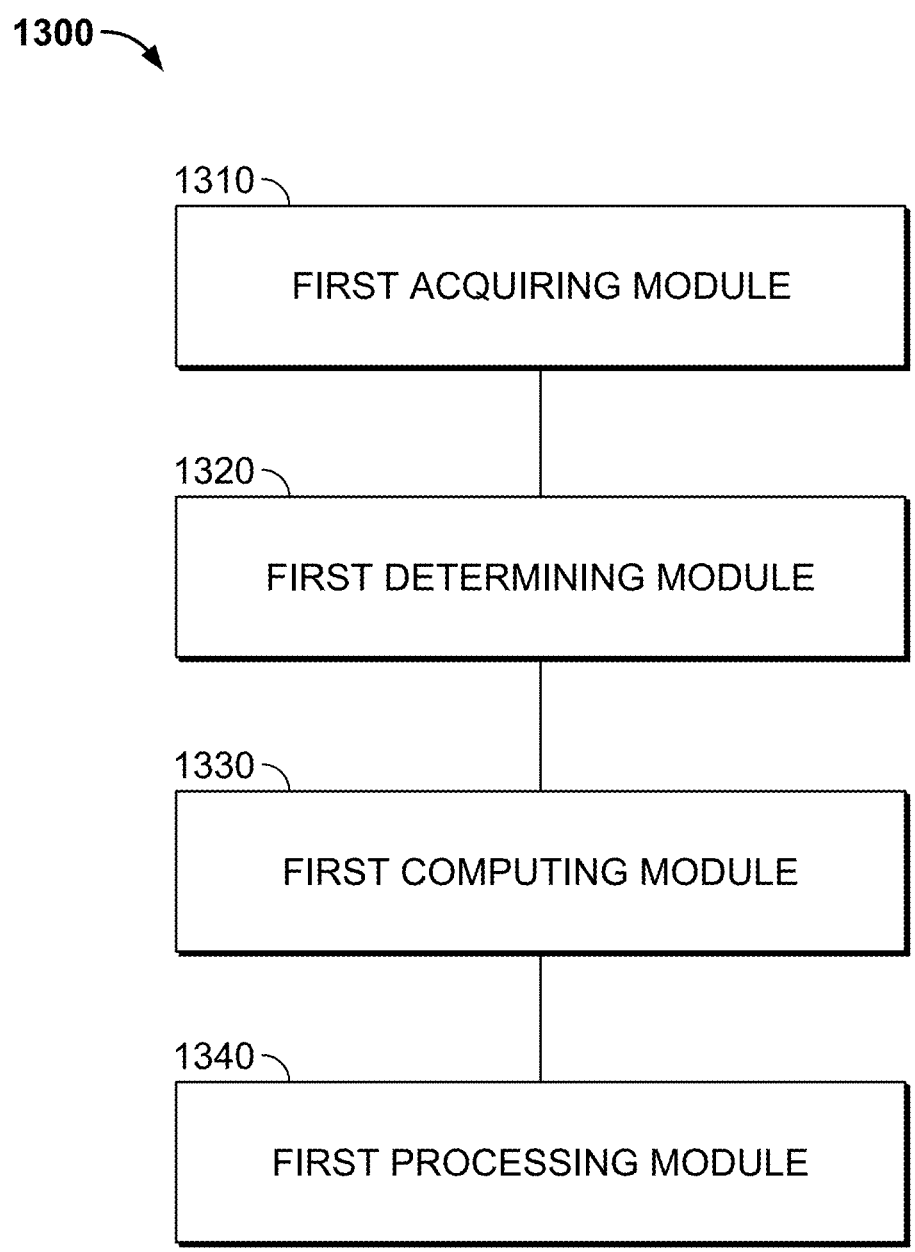
FIG. 13 is a structural diagram of an embodiment of a system for predicting an affinity between a drug and a target.

FIG. 13 is a structural diagram of an embodiment of a system for predicting an affinity between a drug and a target. In some embodiments, the system 1300 is configured to implement process 200 of FIG. 2 and comprises: a first acquiring module 1310, a first determining module 1320, a first computing module 1330, and a first processing module 1340.

In some embodiments, the first acquiring module 1310 is configured to acquire a drug and a target for interacting with the drug.

In some embodiments, the first determining module 1320 is configured to cause an interaction between the drug and the target to determine a compound.

In some embodiments, the first computing module 1330 is configured to compute topological structure graphs for labeling spatial characteristics of atoms in the compound.

In some embodiments, the first processing module 1340 is configured to determine an affinity between the drug and the target based on the topological structure graphs.

In some embodiments, the topological structure graphs include at least one of the following: persistent spectral graph, persistent spectral simplicial complex, change features of the persistent spectral simplicial complex, and/or persistent spectral hypergraph. In some embodiments, the persistent spectral graph labels the persistence and extent of change of topological features, and the persistent spectral hypergraph labels the persistence and extent of change of topological features of a hypergraph.

In some embodiments, the topological structure graph exhibits a nested structure.

In some embodiments, in the event that the first computing module 1330 computes a topological structure graph for labeling spatial characteristics of atoms in a compound, the first computing module 1330 is configured to perform the following: acquiring interaction distances between set atoms in the compound; and determining the topological structure graph for labeling spatial characteristics of atoms in the compound based on the interaction distances.

In some embodiments, in the event that the first computing module 1330 acquires the interaction distances between the set atoms in the compound, the first computing module 1330 is configured to perform the following: acquiring at least one first atom corresponding to the drug and at least one second atom corresponding to the target; computing first coordinates of the at least one first atom and second coordinates of the at least one second atom, and determining the interaction distances between the at least one first atom and the at least one second atom based on the first coordinates and the second coordinates.

In some embodiments, in the event that the first computing module 1330 determines the interaction distances between the at least one first atom and the at least one second atom based on the first coordinates and second coordinates, the first computing module 1330 is configured to perform the following: determining the Euclidean distances between the at least one first atom and the at least one second atom based on the first coordinates and the second coordinates; and determining the Euclidean distances to be the interaction distances between the at least one first atom and the at least one second atom.

In some embodiments, in the event that the first computing module 1330 determines the interaction distances between the at least one first atom and the at least one second atom based on the first coordinates and the second coordinates, the first computing module 1330 is configured to perform the following: acquiring first electric charge information of the at least one first atom and second electric charge information of the at least one second atom; determining electric charge action distance between the at least one first atom and the at least one second atom based on the first coordinates, the second coordinates, the first electric charge information, and the second electric charge information.

In some embodiments, in the event that the first computing module 1330 determines the electric charge action distances between the at least one first atom and the at least one second atom based on the first coordinates, the second coordinates, the first electric charge information, and the second electric charge information, the first computing module 1330 is configured to perform the following: determining the Euclidean distances between the at least one first atom and the at least one second atom based on the first coordinates and the second coordinates; and determining the electric charge action distance between the at least one first atom and the at least one second atom based on the Euclidean distances, the first electric charge information, and the second electric charge information.

In some embodiments, the electric charge action distance is positively related to the first electric charge information, the electric charge action distance is positively related to the second electric charge information, and the electric charge action distance is negatively related to the Euclidean distance.

In some embodiments, in the event, that the first computing module 1330 determines topological structure graphs for labeling spatial characteristics of atoms in the compound based on the interaction distances, the first computing module 1330 is configured to perform the following: acquiring combinatorial Laplacian matrices for labeling spatial characteristics of atoms in the compound based on the interaction distances; and determining the topological structure graphs based on the combinatorial Laplacian matrices.

In some embodiments, in the event that the first processing module 1340 determines the affinity between a drug and a target based on topological structure graphs, the first processing module 1340 is configured to perform the following: acquiring the setting parameter related to the number of persistent spectral simplicial complexes in the topological structure graphs, determining the neural network model corresponding to the setting parameter, and analytically processing, using the neural network model, the topological structure graphs to generate the affinity corresponding to the setting parameter.

In some embodiments, in the event that the first processing module 1340 determines the neural network model corresponding to the setting parameter, the first processing module 1340 is configured to perform the following: in the event that the setting parameter is 0, determining that the neural network model is a first subnetwork model for determining the one-dimensional affinity between the drug and the target; and in the event that the setting parameter is 1, determining that the neural network model is a second subnetwork model for determining the two-dimensional affinity between the drug and the target.

In some embodiments, in the event that the first processing module 1340 analytically processes topological structure graphs based on the neural network model to generate an affinity corresponding to the setting parameter, the first processing module 1340 is configured to perform the following: in the event that the neural network model is a first subnetwork model, analytically processing the topological structure graphs using the first subnetwork model to determine the one-dimensional affinity corresponding to the setting parameter; and in the event that the neural network model is a second subnetwork model, analytically processing the topological structure graphs using the second subnetwork model to determine the two-dimensional affinity corresponding to the setting parameter.

In some embodiments, in the event that the first computing module 1330 computes topological structure graphs for labeling spatial characteristics of atoms in a compound, the first computing module 1330 is configured to perform the following: in the event that the setting parameter is 0, computing first topological structure graphs for labeling spatial characteristics of atoms in a compound; and in the event that the setting parameter is 1, computing second topological structure graphs for labeling spatial characteristics of atoms in a compound. In some embodiments, the number of second topological structure graphs is more than one and corresponds to multiple different observation parameters.

In some embodiments, the topological structure graphs include at least one group; and in the event that the first processing module 1340 determines the affinity between the drug and the target based on the topological structure graphs, the first processing module 1340 is configured to perform the following: analytically processing each group of topological structure graphs using a deep learning model to obtain at least one affinity corresponding to the at least one group of topological structure graphs, wherein the deep learning model is trained to determine the affinities between drugs and targets based on the topological structure graphs; and determining the target affinity between the drug and the target based on the at least one affinity.

In some embodiments, in the event that the first processing module 1340 determines the affinity between the target and the drug based on the at least one affinity, the first processing module 1340 is configured to perform the following: acquiring a weight coefficient corresponding to each of the at least one affinity, calculating the weighted sum of all affinities using the weight coefficients, and obtaining the target affinity between the drug and the target.

In some embodiments, after the weight coefficients corresponding to each of the at least one affinity are acquired, the first processing module 1340 is configured to perform the following: acquiring the actual affinity corresponding to the at least one affinity; and performing an optimization update on the weight coefficients corresponding to each of the at least one affinity using the actual affinity and the at least one affinity to obtain updated weight coefficients.

In some embodiments, in the event that the first processing module 1340 performs an update on the weight coefficients corresponding to each of the at least one affinity using the actual affinity and at least one affinity to obtain updated weight coefficients, the first processing module 1340 is configured to perform the following: acquiring correlation coefficients between at least two affinities and the actual affinity, and performing maximization processing on the correlation coefficients using an optimization function to obtain weight coefficients corresponding to each affinity.

In some embodiments, after the affinity between the drug and the target is determined, the first acquiring module 1310 and the first processing module 1340 are configured to perform the following: the first acquiring module 1310 is configured to acquire the actual affinity between the drug and the target; and the first processing module 1340 is configured to: analytically process the actual affinity and the target affinity using a loss function to determine trainable parameters of the deep learning model; and train the deep learning model based on the trainable parameters to obtain a trained deep learning model.

In some embodiments, the deep learning model comprises a first model for generating a one-dimensional affinity and a second model for generating a two-dimensional affinity. In the event that the first processing module 1340 subjects the deep learning model to optimization training based on the trainable parameters to obtain a trained deep learning model, the first processing module 1340 is configured to perform the following: subjecting the first model to optimization training based on the trainable parameters to obtain a first trained model; subjecting the second model to optimization training based on the trainable parameters to obtain a second trained model; and obtaining a trained deep learning model based on the first trained model and the second trained model.

The modules described above can be implemented as software components executing on one or more general purpose processors, as hardware such as programmable logic devices and/or Application Specific Integrated Circuits designed to perform certain functions or a combination thereof. In some embodiments, the modules can be embodied by a form of software products which can be stored in a nonvolatile storage medium (such as optical disk, flash storage device, mobile hard disk, etc.), including a number of instructions for making a computer device (such as personal computers, servers, network equipment, etc.) implement the methods described in the embodiments of the present invention. The modules may be implemented on a single device or distributed across multiple devices. The functions of the modules may be merged into one another or further split into multiple sub-modules.

The system 1300 as shown in FIG. 13 can be configured to perform any of the processes shown in FIGS. 1-12. In some embodiments, the system 1300 can be implemented as an electronic device. The electronic device can be any of various devices such as a mobile phone, a tablet, or a server.

Figure 14:
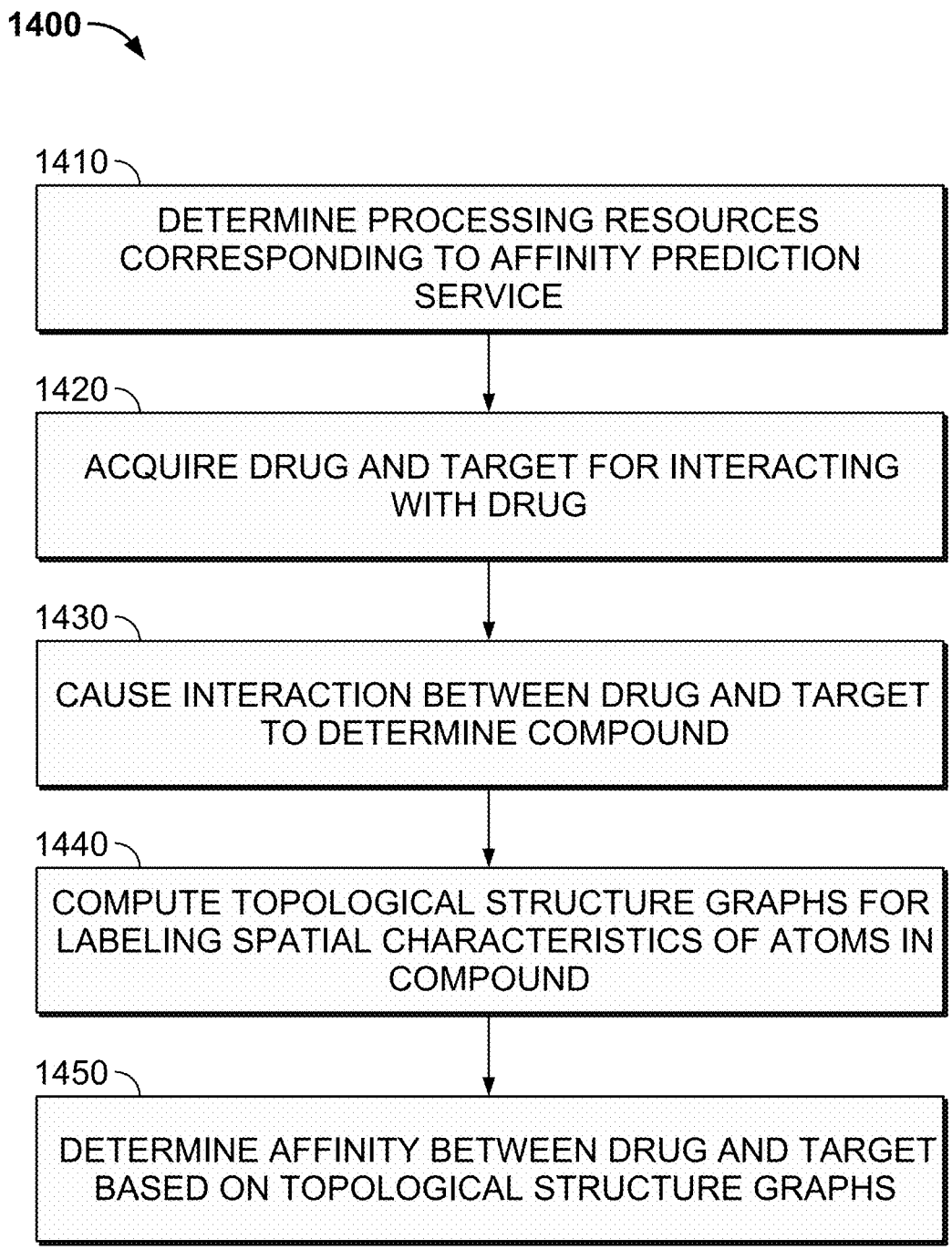
FIG. 14 is a flowchart of another embodiment of a process for predicting an affinity between a drug and a target.

FIG. 14 is a flowchart of another embodiment of a process for predicting an affinity between a drug and a target. In some embodiments, the process 1400 is implemented by system 1600 of FIG. 16 and comprises:

In 1410, in response to receiving an affinity prediction service request, the system determines processing resources corresponding to the affinity prediction service.

In 1420, the system acquires a drug and a target for interacting with the drug using the processing resources.

In 1430, the system causes the interaction between the drug and the target to determine a compound using the processing resources.

In 1440, the system computes topological structure graphs for labeling spatial characteristics of atoms in the compound using the processing resources.

In 1450, the system determines affinity between the drug and the target based on the topological structure graphs using the processing resources.

As an example, the process 1400 for predicting the affinity between a drug and a target can be implemented on a cloud. Several computing nodes can be deployed on the cloud, each computing node having processing resources such as processing resources for computing and storage. Multiple computing nodes can be organized on the cloud to provide a service. In some embodiments, one computing node provides one or more services.

In some embodiments, a cloud provides a service for performing the process 1400 for predicting the affinity between a drug and a target and is called a drug-target affinity prediction service. In the event that a user uses the drug-target affinity prediction service, the drug-target affinity prediction service is called to trigger the cloud into calling a request for the drug-target affinity prediction service. This request can include drug and target information for the prediction. The cloud determines a computing node for responding to the request and performs the following operations using processing resources in the computing node: acquiring a drug and a target for interacting with the drug; causing an interaction between the drug and the target to determine the compound; computing topological structure graphs for labeling spatial characteristics of atoms in the compound; and determining an affinity between the drug and the target based on the topological structure graphs.

As an example, the implementation process, implementation principles, and implementation results of the above process operation correspond to those of the above embodiments shown in FIGS. 1 through 11. One can refer to the relevant explanations of the embodiments shown in FIGS. 1 through 11 regarding aspects of the present embodiment that are not described in detail.

Figure 15:
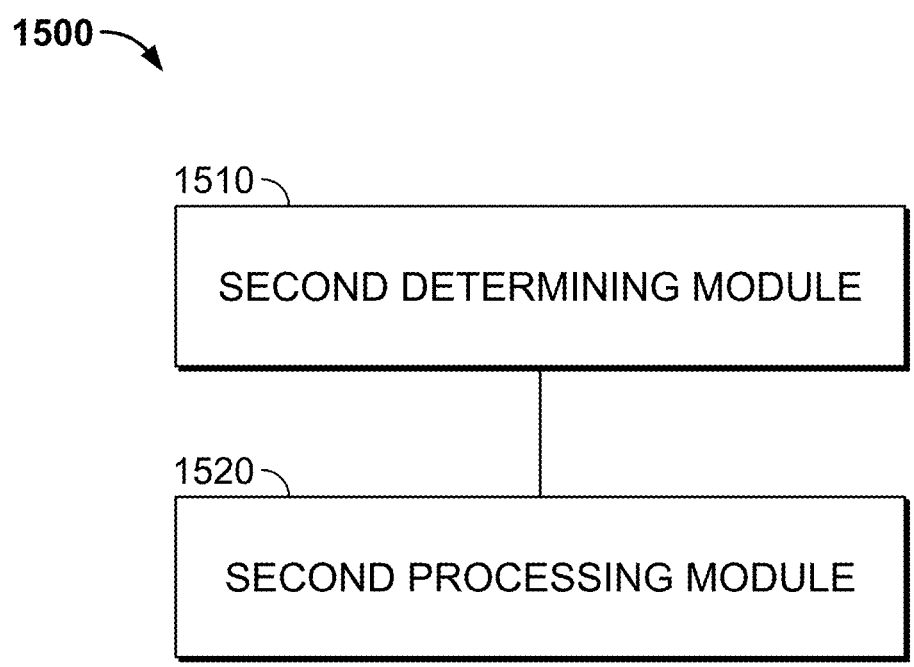
FIG. 15 is a structural diagram of another embodiment of a system for predicting an affinity between a drug and a target.

FIG. 15 is a structural diagram of another embodiment of a system for predicting an affinity between a drug and a target. In some embodiments, the system 1500 is configured to implement process 1400 of FIG. 14 and comprises: a second determining module 1510 and a second processing module 1520.

In some embodiments, the second determining module 1510 is configured to determine processing resources corresponding to an affinity prediction service in response to receiving an affinity prediction service request.

In some embodiments, the second processing module 1520 is configured to acquire a drug and a target for interacting with the drug using the processing resources; cause an interaction between the drug and the target to determine the compound using the processing resources; compute topological structure graphs for labeling spatial characteristics of atoms in the compound using the processing resources; and determine an affinity between the drug and the target based on the topological structure graphs using the processing resources.

Figure 16:
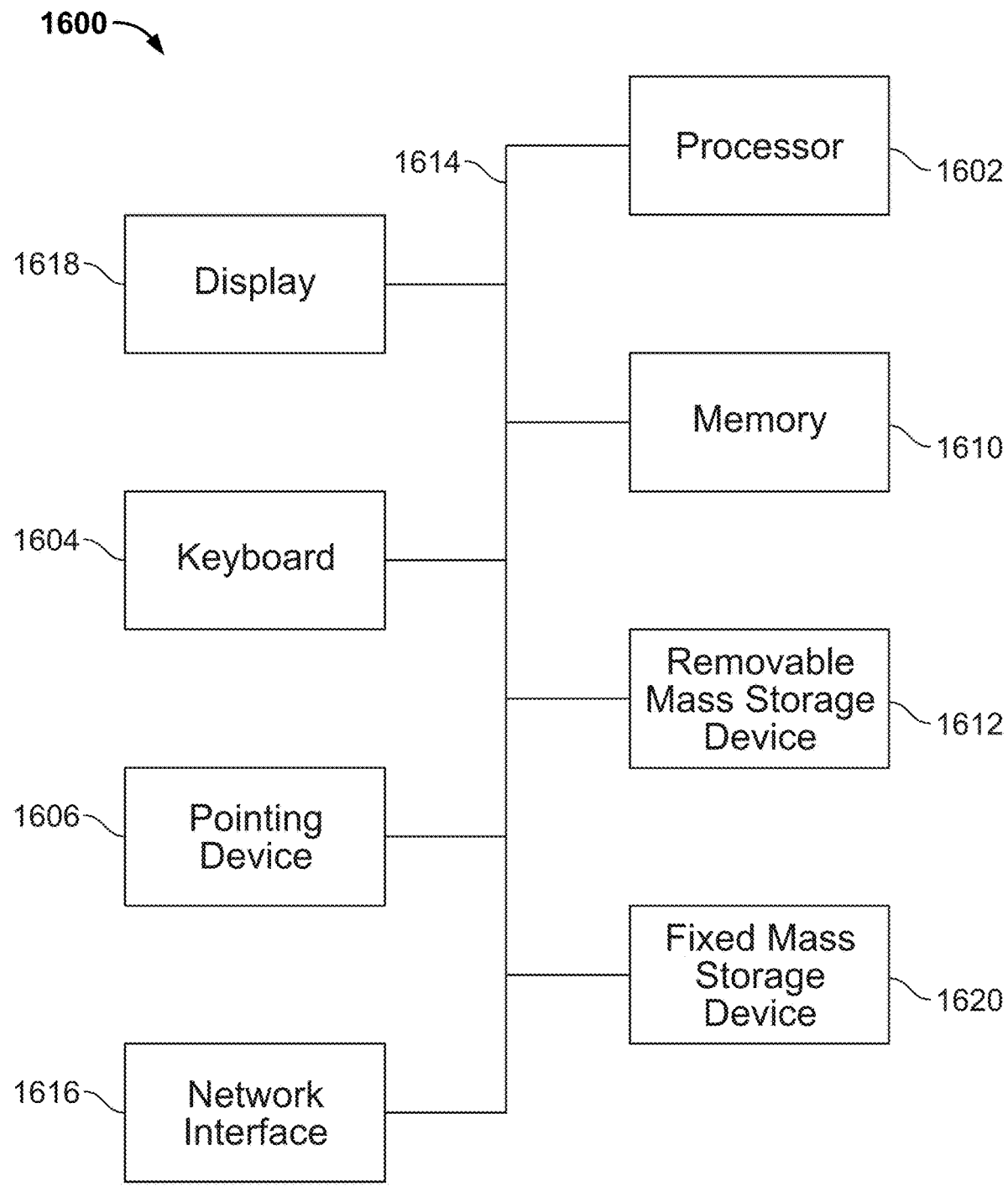
FIG. 16 is a functional diagram illustrating a programmed computer system for predicting an affinity between a drug and a target in accordance with some embodiments.

FIG. 16 is a functional diagram illustrating a programmed computer system for predicting an affinity between a drug and a target in accordance with some embodiments. As will be apparent, other computer system architectures and configurations can be used to generate a molecular structure of a chemical compound. Computer system 1600, which includes various subsystems as described below, includes at least one microprocessor subsystem (also referred to as a processor or a central processing unit (CPU)) 1602. For example, processor 1602 can be implemented by a single-chip processor or by multiple processors. In some embodiments, processor 1602 is a general purpose digital processor that controls the operation of the computer system 1600. Using instructions retrieved from memory 1610, the processor 1602 controls the reception and manipulation of input data, and the output and display of data on output devices (e.g., display 1618). In some embodiments, processor 1602 is configured to predict an affinity between a drug and a target with respect to FIGS. 1-12 and 14.

Processor 1602 is coupled bi-directionally with memory 1610, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 1602. Also as is well known in the art, primary storage typically includes basic operating instructions, program code, data and objects used by the processor 1602 to perform its functions (e.g., programmed instructions). For example, memory 1610 can include any suitable computer-readable storage media, described below, depending on whether, for example, data access needs to be bi-directional or uni-directional. For example, processor 1602 can also directly and very rapidly retrieve and store frequently needed data in a cache memory (not shown).

A removable mass storage device 1612 provides additional data storage capacity for the computer system 1600, and is coupled either bi-directionally (read/write) or unidirectionally (read only) to processor 1602. For example, storage 1612 can also include computer-readable media such as magnetic tape, flash memory, PC-CARDS, portable mass storage devices, holographic storage devices, and other storage devices. A fixed mass storage 1620 can also, for example, provide additional data storage capacity. The most common example of mass storage 1620 is a hard disk drive. Mass storages 1612 and 1620 generally store additional programming instructions, data, and the like that typically are not in active use by the processor 1602. It will be appreciated that the information retained within mass storages 1612 and 1620 can be incorporated, if needed, in standard fashion as part of memory 1610 (e.g., RAM) as virtual memory.

In addition to providing processor 1602 access to storage subsystems, bus 1614 can also be used to provide access to other subsystems and devices. As shown, these can include a display monitor 1618, a network interface 1616, a keyboard 1604, and a pointing device 1606, as well as an auxiliary input/output device interface, a sound card, speakers, and other subsystems as needed. For example, the pointing device 1606 can be a mouse, stylus, track ball, or tablet, and is useful for interacting with a graphical user interface.

The network interface 1616 allows processor 1602 to be coupled to another computer, computer network, or telecommunications network using a network connection as shown. For example, through the network interface 1616, the processor 1602 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 1602 can be used to connect the computer system 1600 to an external network and transfer data according to standard protocols. For example, various process embodiments disclosed herein can be executed on processor 1602, or can be performed across a network such as the Internet, intranet networks, or local area networks, in conjunction with a remote processor that shares a portion of the processing. Additional mass storage devices (not shown) can also be connected to processor 1602 through network interface 1616.

An auxiliary I/O device interface (not shown) can be used in conjunction with computer system 1600. The auxiliary I/O device interface can include general and customized interfaces that allow the processor 1602 to send and, more typically, receive data from other devices such as microphones, touch-sensitive displays, transducer card readers, tape readers, voice or handwriting recognizers, biometrics readers, cameras, portable mass storage devices, and other computers.

The computer system shown in FIG. 16 is but an example of a computer system suitable for use with the various embodiments disclosed herein. Other computer systems suitable for such use can include additional or fewer subsystems. In addition, bus 1614 is illustrative of any interconnection scheme serving to link the subsystems. Other computer architectures having different configurations of subsystems can also be utilized.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:
acquiring a drug and a target for interacting with the drug;
causing an interaction between the drug and the target to determine a compound;
computing topological structure graphs for labeling spatial characteristics of atoms in the compound, wherein the topological structure graphs include at least one group; and
determining an affinity between the drug and the target based on the topological structure graphs, wherein the determining of the affinity between the drug and the target based on the topological structure graphs comprises:
analytically processing each of the at least one group of topological structure graphs using a deep learning model to obtain at least one affinity corresponding to the at least one group of topological structure graphs, wherein the deep learning model is trained to determine affinities between drugs and targets based on the topological structure graphs;
determining a target affinity between the drug and the target based on the at least one affinity, wherein the determining of the target affinity between the drug and the target based on the at least one affinity comprises:
acquiring a weight coefficient corresponding to each of the at least one affinity; and
calculating a weighted sum of all affinities based on weight coefficients to obtain the target affinity between the drug and the target;
acquiring an actual affinity corresponding to the at least one affinity; and
performing an update on the weight coefficient corresponding to each of the at least one affinity using the actual affinity and the at least one affinity to obtain updated weight coefficients, wherein the performing of the update on the weight coefficients corresponding to each of the at least one affinity to obtain the updated weight coefficients comprises:
acquiring correlation coefficients between at least two affinities and the actual affinity; and
performing maximization processing on the correlation coefficients to obtain optimized weight coefficients corresponding to each of the at least one affinity using an optimization function.

2. The method as described in claim 1, wherein:
the topological structure graphs include at least one of the following: a persistent spectral graph, a persistent spectral simplicial complex, change features of the persistent spectral simplicial complex, and/or a persistent spectral hypergraph;
the persistent spectral graph is configured to label persistence and extent of change of topological features; and
the persistent spectral hypergraph is configured to label persistence and extent of change of topological features of a hypergraph.

3. The method as described in claim 2, wherein the topological structure graphs exhibit a nested structure.

4. The method as described in claim 1, wherein the computing of the topological structure graphs for labeling the spatial characteristics of the atoms in the compound comprises:
acquiring interaction distances between set atoms in the compound; and
determining the topological structure graphs for labeling the spatial characteristics of the atoms in the compound based on the interaction distances.

5. The method as described in claim 4, wherein the acquiring of the interaction distances between the set atoms in the compound comprises:
acquiring at least one first atom corresponding to the drug and at least one second atom corresponding to the target;
calculating first coordinates of the at least one first atom and second coordinates of the at least one second atom; and
determining the interaction distances between the at least one first atom and the at least one second atom based on the first coordinates and the second coordinates.

6. The method as described in claim 5, wherein the determining of the interaction distances between the at least one first atom and the at least one second atom based on the first coordinates and the second coordinates comprises:
determining Euclidean distances between the at least one first atom and the at least one second atom based on the first coordinates and the second coordinates; and
determining the Euclidean distances to be the interaction distances between the at least one first atom and the at least one second atom.

7. The method as described in claim 5, wherein the determining of the interaction distances between the at least one first atom and the at least one second atom based on the first coordinates and the second coordinates comprises:
acquiring first electric charge information of the at least one first atom and second electric charge information of the at least one second atom; and
determining electric charge action distances between the at least one first atom and the at least one second atom based on the first coordinates, the second coordinates, the first electric charge information, and the second electric charge information.

8. The method as described in claim 7, wherein the determining of the electric charge action distances between the at least one first atom and the at least one second atom based on the first coordinates, the second coordinates, the first electric charge information, and the second electric charge information comprises:
determining Euclidean distances between the at least one first atom and the at least one second atom based on the first coordinates and the second coordinates; and
determining the electric charge action distances between the at least one first atom and the at least one second atom based on the Euclidean distances, the first electric charge information, and the second electric charge information.

9. The method as described in claim 8, wherein an electric charge action distance is positively related to the first electric charge information, an electric charge action distance is positively related to the second electric charge information, and an electric charge action distance is negatively related to a Euclidean distance.

10. The method as described in claim 4, wherein the determining of the topological structure graphs for labeling the spatial characteristics of the atoms in the compound based on the interaction distances comprises:

acquiring combinatorial Laplacian matrices for labeling the spatial characteristics of the atoms in the compound based on the interaction distances; and determining the topological structure graphs based on the combinatorial Laplacian matrices.

11. The method as described in claim 1, wherein the determining of the affinity between the drug and the target based on the topological structure graphs comprises:

acquiring a setting parameter related to a number of persistent spectral simplicial complexes in the topological structure graphs;

determining a neural network model corresponding to the setting parameter; and analytically processing the topological structure graphs using the neural network model to generate the affinity corresponding to the setting parameter.

12. The method as described in claim 11, wherein the determining of the neural network model corresponding to the setting parameter comprises:

in the event that the setting parameter is 0, determining the neural network model to be a first subnetwork model for determining one-dimensional affinity between the drug and the target; and in the event that the setting parameter is 1, determining the neural network model to be a second subnetwork model for determining two-dimensional affinity between the drug and the target.

13. The method as described in claim 12, wherein the analytically processing of the topological structure graphs using the neural network model to generate the affinity corresponding to the setting parameter comprises:

in the event that the neural network model is a first subnetwork model, analytically processing the topological structure graphs using the first subnetwork model to determine the one-dimensional affinity corresponding to the setting parameter; and in the event that the neural network model is a second subnetwork model, analytically processing the topological structure graphs using the second subnetwork model to determine the two-dimensional affinity corresponding to the setting parameter.

14. The method as described in claim 12, wherein the computing of the topological structure graphs for labeling the spatial characteristics of the atoms in the compound comprises:

in the event that the setting parameter is 0, computing first topological structure graphs for labeling the spatial characteristics of the atoms in the compound; and in the event that the setting parameter is 1, computing second topological structure graphs for labeling the spatial characteristics of the atoms in the compound, the second topological structure graphs being more than one and corresponding to multiple observation parameters.

15. A method, comprising:

acquiring a drug and a target for interacting with the drug;

causing an interaction between the drug and the target to determine a compound;

computing topological structure graphs for labeling spatial characteristics of atoms in the compound, wherein the topological structure graphs includes at least one group; and determining an affinity between the drug and the target based on the topological structure graphs, wherein the determining of the affinity between the drug and the target based on the topological structure graphs comprises:

analytically processing each of the at least one group of the topological structure graphs using a deep learning model to obtain at least one affinity corresponding to the at least one group of topological structure graphs, wherein the deep learning model is trained to determine affinities between drugs and targets based on the topological structure graphs;

determining a target affinity between the drug and the target based on the at least one affinity, wherein the determining of the target affinity between the drug and the target based on the at least one affinity comprises:

acquiring a weight coefficient corresponding to each of the at least one affinity;

calculating a weighted sum of all affinities based on weight coefficients to obtain the target affinity between the drug and the target;

acquiring an actual affinity corresponding to the at least one affinity; and performing an update on the weight coefficient corresponding to each of the at least one affinity using the actual affinity and the at least one affinity to obtain updated weight coefficients;

acquiring the actual affinity between the drug and the target;

analytically processing the actual affinity and the target affinity using a loss function to determine trainable parameters for the deep learning model; and training the deep learning model based on the trainable parameters to obtain a trained deep learning model, wherein:

the deep learning model comprises a first model for generating one-dimensional affinities and a second model for generating two-dimensional affinities; and the training of the deep learning model based on the trainable parameters to obtain the trained deep learning model comprises:

training the first model based on the trainable parameters to obtain a first trained model;

training the second model based on the trainable parameters to obtain a second trained model; and obtaining the trained deep learning model based on the first trained model and the second trained model.

16. A system, comprising:

a processor; and a memory coupled with the processor, wherein the memory is configured to provide the processor with instructions which when executed cause the processor to:

acquire a drug and a target for interacting with the drug;

cause an interaction between the drug and the target to determine a compound;

compute topological structure graphs for labeling spatial characteristics of atoms in the compound, wherein the topological structure graphs include at least one group; and determine an affinity between the drug and the target based on the topological structure graphs, wherein the determining of the affinity between the drug and the target based on the topological structure graphs comprises to:

analytically process each of the at least one group of topological structure graphs using a deep learning model to obtain at least one affinity corresponding to the at least one group of topological structure graphs, wherein the deep learning model is trained to determine affinities between drugs and targets based on the topological structure graphs;
determine a target affinity between the drug and the target based on the at least one affinity, wherein the determining of the target affinity between the drug and the target based on the at least one affinity comprises to:
acquire a weight coefficient corresponding to each of the at least one affinity; and
calculate a weighted sum of all affinities based on weight coefficients to obtain the target affinity between the drug and the target;
acquire an actual affinity corresponding to the at least one affinity; and
perform an update on the weight coefficient corresponding to each of the at least one affinity using the actual affinity and the at least one affinity to obtain updated weight coefficients, wherein the performing of the update on the weight coefficients corresponding to each of the at least one affinity to obtain the updated weight coefficients comprises to:
acquire correlation coefficients between at least two affinities and the actual affinity; and
perform maximization processing on the correlation coefficients to obtain optimized weight coefficients corresponding to each of the at least one affinity using an optimization function.

17. A computer program product being embodied in a tangible non-transitory computer readable storage medium and comprising computer instructions for:
acquiring a drug and a target for interacting with the drug;
causing an interaction between the drug and the target to determine a compound;
computing topological structure graphs for labeling spatial characteristics of atoms in the compound, wherein the topological structure graphs include at least one group; and
determining an affinity between the drug and the target based on the topological structure graphs, wherein the determining of the affinity between the drug and the target based on the topological structure graphs comprises:
analytically processing each of the at least one group of topological structure graphs using a deep learning model to obtain at least one affinity corresponding to the at least one group of topological structure graphs, wherein the deep learning model is trained to determine affinities between drugs and targets based on the topological structure graphs;
determining a target affinity between the drug and the target based on the at least one affinity, wherein the determining of the target affinity between the drug and the target based on the at least one affinity comprises:
acquiring a weight coefficient corresponding to each of the at least one affinity; and
calculating a weighted sum of all affinities based on weight coefficients to obtain the target affinity between the drug and the target;
acquiring an actual affinity corresponding to the at least one affinity; and
performing an update on the weight coefficient corresponding to each of the at least one affinity using the actual affinity and the at least one affinity to obtain updated weight coefficients, wherein the performing of the update on the weight coefficients corresponding to each of the at least one affinity to obtain the updated weight coefficients comprises:
acquiring correlation coefficients between at least two affinities and the actual affinity; and
performing maximization processing on the correlation coefficients to obtain optimized weight coefficients corresponding to each of the at least one affinity using an optimization function.

18. A system, comprising:
a processor; and
a memory coupled with the processor, wherein the memory is configured to provide the processor with instructions which when executed cause the processor to:
acquire a drug and a target for interacting with the drug;
cause an interaction between the drug and the target to determine a compound
compute topological structure graphs for labeling spatial characteristics of atoms in the compound, wherein the topological structure graphs include at least one group; and
determine an affinity between the drug and the target based on the topological structure graphs, wherein the determining of the affinity between the drug and the target based on the topological structure graphs comprises to:
analytically process each of the at least one group of topological structure graphs using a deep learning model to obtain at least one affinity corresponding to the at least one group of topological structure graphs, and wherein the deep learning model is trained to determine affinities between drugs and targets based on the topological structure graphs;
determine a target affinity between the drug and the target based on the at least one affinity, wherein the determining of the target affinity between the drug and the target based on the at least one affinity comprises to:
acquire a weight coefficient corresponding to each of the at least one affinity;
calculate a weighted sum of all affinities based on weight coefficients to obtain the target affinity between the drug and the target;
acquire an actual affinity corresponding to the at least one affinity; and
perform an update on the weight coefficient corresponding to each of the at least one affinity using the actual affinity and the at least one affinity to obtain updated weight coefficients;
acquire the actual affinity between the drug and the target;
analytically process the actual affinity and the target affinity using a loss function to determine trainable parameters for the deep learning model; and
train the deep learning model based on the trainable parameters to obtain a trained deep learning model, wherein:
the deep learning model comprises a first model for generating one-dimensional affinities and a second model for generating two-dimensional affinities; and
the training of the deep learning model based on the trainable parameters to obtain the trained deep learning model comprises to:

train the first model based on the trainable parameters to obtain a first trained model;
train the second model based on the trainable parameters to obtain a second trained model; and
obtain the trained deep learning model based on the first trained model and the second trained model.

19. A computer program product being embodied in a tangible non-transitory computer readable storage medium and comprising computer instructions for:
acquiring a drug and a target for interacting with the drug;
causing an interaction between the drug and the target to determine a compound;
computing topological structure graphs for labeling spatial characteristics of atoms in the compound, wherein the topological structure graphs includes at least one group; and
determining an affinity between the drug and the target based on the topological structure graphs, wherein the determining of the affinity between the drug and the target based on the topological structure graphs comprises:
analytically processing each of the at least one group of the topological structure graphs using a deep learning model to obtain at least one affinity corresponding to the at least one group of topological structure graphs, wherein the deep learning model is trained to determine affinities between drugs and targets based on the topological structure graphs;
determining a target affinity between the drug and the target based on the at least one affinity, wherein the determining of the target affinity between the drug and the target based on the at least one affinity comprises:
acquiring a weight coefficient corresponding to each of the at least one affinity;
calculating a weighted sum of all affinities based on weight coefficients to obtain the target affinity between the drug and the target;
acquiring an actual affinity corresponding to the at least one affinity; and
performing an update on the weight coefficient corresponding to each of the at least one affinity using the actual affinity and the at least one affinity to obtain updated weight coefficients;
acquiring the actual affinity between the drug and the target;
analytically processing the actual affinity and the target affinity using a loss function to determine trainable parameters for the deep learning model; and
training the deep learning model based on the trainable parameters to obtain a trained deep learning model, wherein:
the deep learning model comprises a first model for generating one-dimensional affinities and a second model for generating two-dimensional affinities; and
the training of the deep learning model based on the trainable parameters to obtain the trained deep learning model comprises:
training the first model based on the trainable parameters to obtain a first trained model;
training the second model based on the trainable parameters to obtain a second trained model; and
obtaining the trained deep learning model based on the first trained model and the second trained model.

* * * * *